United States Patent
Kaemmerer

(10) Patent No.: US 9,861,821 B2
(45) Date of Patent: Jan. 9, 2018

(54) THERAPEUTIC WINDOW DETERMINATION

(71) Applicant: Medtronic, Inc., Minneapolis, MN (US)

(72) Inventor: William F. Kaemmerer, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/259,865

(22) Filed: Sep. 8, 2016

(65) Prior Publication Data

US 2016/0375253 A1 Dec. 29, 2016

Related U.S. Application Data

(63) Continuation of application No. 14/195,489, filed on Mar. 3, 2014, now Pat. No. 9,457,188.

(51) Int. Cl.
- *A61N 1/00* (2006.01)
- *A61N 1/36* (2006.01)
- *A61N 1/372* (2006.01)

(52) U.S. Cl.
CPC ..... *A61N 1/36139* (2013.01); *A61N 1/36142* (2013.01); *A61N 1/37247* (2013.01)

(58) Field of Classification Search
USPC .......................................................... 607/59
See application file for complete search history.

(56) References Cited

U.S. PATENT DOCUMENTS

| 7,386,348 B2 | 6/2008 | North et al. |
| 7,623,918 B2 | 11/2009 | Goetz |

(Continued)

FOREIGN PATENT DOCUMENTS

| CN | 103501855 A | 1/2014 |
| WO | 2011084341 A1 | 7/2011 |

(Continued)

OTHER PUBLICATIONS

Beriault et al., "Towards Computer-Assisted Deep Brain Stimulation Targeting with Multiple Active Contacts," MICCAI International Conference on Medical Image Computing and Computer-Assisted Intervention, McConnell Brain Imagine Centre, Montreal Neurological Institute, Jan. 2012, 8 pp.

(Continued)

*Primary Examiner* — Nicole F Johnson
(74) *Attorney, Agent, or Firm* — Shumaker & Sieffert, P.A.

(57) ABSTRACT

A therapeutic window for at least one electrode of a medical system may be determined based on a volume of tissue expected to be activated ("VTA") by electrical stimulation delivered by the at least one electrode. In some examples, a processor determines the therapeutic window for a particular electrode by at least determining an efficacy threshold based on the VTA expected to result from the delivery of electrical stimulation according to a set of electrical stimulation parameter values including the stimulation parameter at the efficacy threshold, and determining an adverse-effects threshold based on the VTA expected to result from the delivery of electrical stimulation according to a set of electrical stimulation parameter values including the stimulation parameter at the adverse-effects threshold.

34 Claims, 7 Drawing Sheets

(56) References Cited

U.S. PATENT DOCUMENTS

| | | |
|---|---|---|
| 7,657,319 B2 | 2/2010 | Goetz et al. |
| 7,822,483 B2 | 10/2010 | Stone et al. |
| 8,180,601 B2 | 5/2012 | Butson et al. |
| 8,326,433 B2 | 12/2012 | Blum et al. |
| 8,379,952 B2 | 2/2013 | McIntyre et al. |
| 8,433,414 B2 | 4/2013 | Gliner et al. |
| 8,583,230 B2 | 11/2013 | Ryu et al. |
| 8,914,119 B2 | 12/2014 | Wu et al. |
| 2006/0017749 A1 | 1/2006 | McIntyre et al. |
| 2009/0281596 A1 | 11/2009 | King et al. |
| 2009/0287271 A1 | 11/2009 | Blum et al. |
| 2010/0256438 A1 | 10/2010 | Mishelevich et al. |
| 2011/0040352 A1 | 2/2011 | Gerber et al. |
| 2011/0040546 A1 | 2/2011 | Gerber et al. |
| 2011/0307032 A1 | 12/2011 | Goetz et al. |
| 2012/0014580 A1 | 1/2012 | Blum et al. |
| 2012/0185012 A1* | 7/2012 | Ryu ................ A61N 1/3627 607/25 |
| 2012/0265267 A1 | 10/2012 | Blum et al. |
| 2012/0277621 A1* | 11/2012 | Gerber ............ A61B 5/0031 600/554 |
| 2012/0303089 A1 | 11/2012 | Martens et al. |
| 2013/0289380 A1 | 10/2013 | Molnar et al. |

FOREIGN PATENT DOCUMENTS

| | | |
|---|---|---|
| WO | 2012145265 A1 | 10/2012 |
| WO | 2013012948 A1 | 1/2013 |

OTHER PUBLICATIONS

Gross et al., "The Clinical Utility of Methods to Determine Spatial Extent and Volume of Tissue Activated by Deep Brain Stimulation," Clinical Neurophisiology, vol. 119(9), Sep. 2008, pp. 1947-1950.

International Search Report and Written Opinion from counterpart International Patent Application No. PCT/US2014/068378, dated Feb. 27, 2015, 12 pp.

International Preliminary Report on Patentability from International Application No. PCT/US2014/068378 dated Sep. 6, 2016, 8 pp.

Prosecution History from U.S. Pat. No. 9,457,489, dated May 20, 2015 through Sep. 2, 2016, 72 pp.

Notice of First Office Action, and English translation thereof, from counterpart Chinese Application No. 201480078376.2, dated Jun. 7, 2017, 16 pp.

Notice of Intent to Grant and text intended for grant from counterpart European Patent Application No. 14816056.7, dated Oct. 20, 2017, 139 pp.

* cited by examiner

THERAPEUTIC WINDOW DETERMINATION

This application is a continuation of U.S. patent application Ser. No. 14/195,489, entitled, "THERAPEUTIC WINDOW DETERMINATION," which was filed on Mar. 3, 2014 and issued on Oct. 4, 2016 as U.S. Pat. No. 9,457,188. The entire content of U.S. patent application Ser. No. 14/195,489 is incorporated herein by reference.

TECHNICAL FIELD

The disclosure relates to electrical stimulation therapy.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. In some therapy systems, an implantable electrical stimulator delivers electrical therapy to a target tissue site within a patient with the aid of one or more electrodes, which may be deployed by medical leads, on a housing of the electrical stimulator, or both.

During a programming session, which may occur during implant of the medical device, during a trial session, or during an in-clinic or remote follow-up session after the medical device is implanted in the patient, a clinician may generate one or more therapy programs (also referred to as therapy parameter sets) that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples in which electrical stimulation is delivered in the form of electrical pulses, for example, the therapy parameters may include an electrode combination, an amplitude, which may be a current or voltage amplitude, a pulse width, and a pulse rate.

SUMMARY

The disclosure describes example systems, devices, and methods for determining, for at least one electrode of a medical system, a range of electrical stimulation parameter values that may provide efficacious therapy to a patient when electrical stimulation is delivered to the patient with the at least one electrode. The range of electrical stimulation parameter values may also be referred to as a therapeutic window. In some examples, a therapeutic window is defined as the values of an electrical stimulation parameter between an efficacy threshold, which may be the lowest electrical stimulation parameter value (or highest, depending on the parameter) at which efficacious effects of the electrical stimulation were first observed, and an adverse-effects threshold, which may be the lowest electrical stimulation parameter value (or highest, depending on the parameter) at which adverse effects of the electrical stimulation were first observed. In some examples, the therapeutic window includes the efficacy threshold, but does not include the adverse-effects threshold.

In some examples, a processor of a device (e.g., a medical device programmer or a medical device) determines the therapeutic window for an electrode based on a volume of tissue expected to be activated by electrical stimulation delivered by the electrode, which may also be referred to as a volume of tissue activation ("VTA"). The processor may determine a VTA for a particular electrode and a set of electrical stimulation parameter values using a modeling algorithm that is based on characteristics of the tissue of the patient proximate the one or more electrodes. In this way, the VTA may be estimated. In some examples, the processor automatically determines the therapeutic window for a particular electrode by at least determining a first value of an electrical stimulation parameter at which a VTA is expected to first overlap with one or more regions of tissue of the patient associated with efficacious electrical stimulation therapy. The overlap may be, for example, overlap sufficient to cause one or more efficacious effects of electrical stimulation. This first value may be an efficacy threshold value. The processor may also automatically determine a second value of the electrical stimulation parameter at which a VTA is expected to first overlap with one or more regions of tissue of the patient associated with one or more adverse effects of electrical stimulation therapy. The overlap may be, for example, overlap sufficient to cause one or more adverse effects of electrical stimulation. This second value may be an adverse-effects threshold.

In accordance with some examples, a therapeutic window is determined for each electrode of a plurality of electrodes of a lead. The plurality of determined therapeutic windows may help a clinician determine which electrodes to use in programming the electrical stimulation therapy for the patient, e.g., which electrodes may provide efficacious therapy with relatively minimal side effects.

In one example, the disclosure is directed to a method comprising determining, by a processor, an efficacy threshold value of at least one electrical stimulation parameter based a first volume of tissue activation expected to result from delivery of electrical stimulation by at least one electrode to a patient, and determining, by the processor, an adverse-effects threshold value of the at least one stimulation parameter based on second volume of tissue activation expected to result from delivery of electrical stimulation by the at least one electrode to the patient.

In another example, the disclosure is directed to a system comprising a memory, and a processor configured to determine an efficacy threshold value of at least one stimulation parameter based a volume of tissue activation expected to result from delivery of electrical stimulation by at least one electrode to a patient, to determine an adverse-effects threshold value of the at least one stimulation parameter based on second volume of tissue activation expected to result from delivery of electrical stimulation by the at least one electrode to the patient, and to store the efficacy threshold value and the adverse-effects threshold value in the memory.

In another example, the disclosure is directed to a system comprising means for determining an efficacy threshold value of at least one electrical stimulation parameter based a first volume of tissue activation expected to result from delivery of electrical stimulation by at least one electrode to a patient, and means for determining an adverse-effects threshold value of the at least one stimulation parameter based on second volume of tissue activation expected to result from delivery of electrical stimulation by the at least one electrode to the patient.

In another example, the disclosure is directed to a computer-readable medium comprising instructions that, when executed, cause a processor to determine an efficacy threshold value of at least one electrical stimulation parameter based a first volume of tissue activation expected to result from delivery of electrical stimulation by at least one electrode to a patient, and determine an adverse-effects threshold value of the at least one stimulation parameter based on a second volume of tissue activation expected to result from delivery of electrical stimulation by the at least one electrode to the patient.

In another aspect, the disclosure is directed to a computer-readable storage medium, which may be an article of manufacture. The computer-readable storage medium includes computer-readable instructions for execution by one or more processors. The instructions cause one or more processors to perform any part of the techniques described herein. The instructions may be, for example, software instructions, such as those used to define a software or computer program.

The details of one or more examples are set forth in the accompanying drawings and the description below. Other features, objects, and advantages will be apparent from the description and drawings, and from the claims.

DETAILED DESCRIPTION

Figure 1:
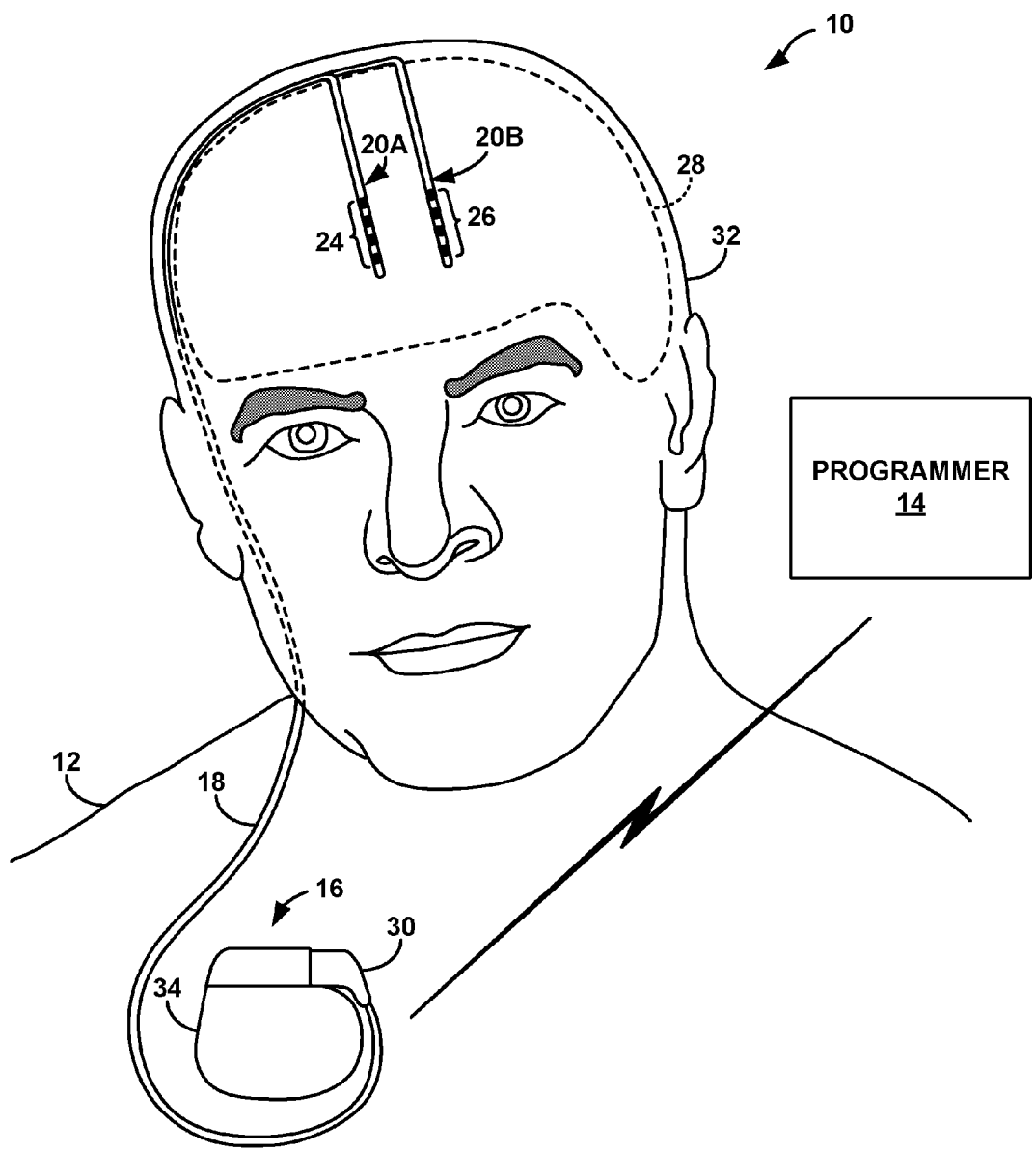
FIG. 1 is a conceptual diagram illustrating an example deep brain stimulation (DBS) system configured to sense a bioelectrical brain signal and deliver electrical stimulation therapy to a tissue site within a brain of a patient.

The disclosure describes example systems, devices, and methods for determining, for at least one electrode of a medical system, a therapeutic window based on a volume of tissue expected to be activated by electrical stimulation delivered via the at least one electrode. The at least one electrode can be, for example, an electrode of a lead or a medical device housing. In some examples, an electrode may also be referred to as a "contact" or an "electrical contact." In some examples, tissue may be "activated" when the electrical stimulation causes an action potential to propagate along a neuron of the tissue, which may indicate that the transmembrane potential of the neuron reached a particular level, such as a potential greater than 0 mV.

The therapeutic window may be a range of values for one or more electrical stimulation parameters, where therapy delivery in accordance with the values within the range may provide efficacious therapy to the patient. In some examples, a therapeutic window is defined as the values of an electrical stimulation parameter between an efficacy threshold value (also referred to herein as an "efficacy threshold") and an adverse-effects threshold value (also referred to herein as an "adverse-effects threshold." In some examples, the lower bound of the therapeutic window may include the efficacy threshold, and the upper bound may be defined by, but not include, the adverse-effects threshold. In other examples, the lower bound of the therapeutic window includes the efficacy threshold and the upper bound includes the adverse-effects threshold. In yet other examples, the upper bound of the therapeutic window may be defined by the efficacy threshold and the lower bound may be defined by the adverse-effects threshold. In these examples, the upper bound may, or may not, include the efficacy threshold.

An efficacy threshold may be the electrical stimulation parameter value at which the electrical stimulation therapy may first yield some efficacy, e.g., as the parameter value is increased or decreased, for the patient and an adverse-effects threshold may be the first electrical stimulation parameter value at which the electrical stimulation therapy may first yield an adverse effect for the patient, e.g., as the parameter value is increased or decreased. The results indicative of efficacy can include, for example, a decrease in the severity, frequency, or both, of one or more symptoms of the patient condition for which the therapy system is implemented to address. Adverse effects can include, for example, any side effect or non-therapeutic effect that the patient or clinician may consider to adversely impact the benefits of the therapy delivery. For example, depending on the patient condition, adverse effects can include muscle contractions or other undesirable muscle recruitment, discomfort, tremors, paresthesia in one or more parts of the body of the patient, and the like.

In some examples described herein, a processor of a device (e.g., a medical device programmer) determines the therapeutic window for a particular electrode by at least determining an efficacy threshold based on the VTA expected to result from the delivery of electrical stimulation according to a set of electrical stimulation parameter values including the stimulation parameter at the efficacy threshold, and determining the adverse-effects threshold based on the VTA expected to result from the delivery of electrical stimulation according to a set of electrical stimulation parameter values including the stimulation parameter at the adverse-effects threshold.

For example, for a particular electrode, the processor may determine an initial VTA based on a set of electrical stimulation parameter values, where the initial VTA is a starting point for the determination of the therapeutic window. The processor may then adjust (e.g., increase or decrease in predetermined increments) the value of at least one of the stimulation parameters of the set until the resulting VTA overlaps with one or more regions of tissue within the patient associated with efficacious results, e.g., in an amount sufficient to cause the efficacious effects. This value may be the efficacy threshold, and the regions of tissue may be referred to as efficacy regions. The processor may then continuing adjusting the value of the at least one stimulation parameter (e.g., in predetermined increments) until the resulting VTA overlaps with one or more regions of tissue within the patient associated with adverse effects, e.g., in an amount sufficient to cause the adverse effects. This value may be the adverse-effects threshold, and the regions of tissue may be referred to as adverse-effects regions. The efficacy regions and adverse-effects regions may be three-dimensional regions (e.g., volumes) of tissue.

The amount of commonality in space between the VTA and the one or more regions of tissue required to constitute an overlap, as the term is used herein, may differ based on various factors, including the region of tissue to which electrical stimulation is applied. For example, an overlap may more than a mere point (e.g., a square millimeter) in common between the VTA and the one or more regions of tissue. Thus, in some cases, the overlap may also be referred to as a "sufficient" overlap, in that the overlap is in an amount sufficient to cause the efficacious effects or adverse effects, or a "significant overlap," in that the overlap is significant enough to cause the efficacious effects or adverse effects. Thus, while the term "overlap" is primarily referred to herein, the discussed overlap can also refer to a sufficient overlap or a significant overlap.

Example efficacy and adverse-effects regions of tissue can include, for example, anatomical structures of the brain, specific muscles or muscle groups, clinician-defined regions of the patient's body, e.g., adjacent the spinal cord or peripheral nerves, and the like. As discussed in further detail below, the one or more regions of tissue used to determine the therapeutic windows may be selected based on information specific to the patient or to a group of patients.

The one or more efficacy regions may include tissue that, when activated by electrical stimulation, elicits a therapeutic benefit or result for the patient, e.g., by mitigating one or more symptoms of a patient condition, reducing a frequency of the occurrence of one or more symptoms or patient events associated with the patient condition, or both. The particular therapeutic benefit or result that is used to determine the efficacious results may differ based on the patient condition or the patient or clinician preferences. If there are multiple efficacy regions with which the VTA is compared to determine whether there is overlap, the regions may be directly adjacent to each other in some examples, e.g., depending on the patient condition, and may be separated by one or more other regions of tissue in other examples.

The one or more adverse-effects regions of tissue may include tissue that, when activated by electrical stimulation, causes one or more side effects. The particular adverse effects that are used to determine the second region may also differ based on the patient condition or the patient or clinician preferences. As with the efficacy regions, if there are multiple adverse-effects regions of tissue, the regions may be directly adjacent to each other in some examples, and may be separated by one or more other regions of tissue in other examples.

In some examples, a processor automatically determines the therapeutic window for each electrode of a plurality of electrodes based on the volume of tissue expected to be activated by electrical stimulation delivered via the respective electrode in a unipolar stimulation configuration. In a unipolar configuration, the active electrode with which electrical stimulation signals are delivered is referenced to an electrode carried by the implantable medical device housing or "can." The processor may associate the therapeutic windows with the respective electrodes in a memory. In some examples, the processor may generate a graphical user interface that includes a list of electrodes and the respective therapeutic windows, or, in some examples, a list of electrodes and the respective efficacy thresholds and adverse-effects threshold.

As part of the programming of an electrical stimulation therapy system, a clinician may select one or more electrode combinations that may provide efficacious therapy to a patient. The electrodes of the electrode combinations may, for example, be selected based on a proximity to a target therapy delivery site, based on a distance from one or more adverse-effects regions of tissue, or both. Therapeutic windows of electrodes may provide a basis for comparing the potential benefits of a plurality of electrodes. For example, the therapeutic window of a particular electrode may indicate whether the electrode may be useful for providing efficacious stimulation therapy to a patient, e.g., by indicating the electrodes that may provide a relatively high efficacy and relative low risk of side effects. Thus, information indicating the therapeutic windows for a plurality of electrodes may help aid the selection of one or more electrode combinations that may provide efficacious electrical stimulation therapy to a patient. For example, an electrode associated with a relatively large therapeutic window (e.g., as indicated by the difference between the electrical stimulation parameter values bounding the therapeutic window) may indicate that the electrode will provide more latitude to find efficacious electrical stimulation parameter values for the patient. Determination of a therapeutic window in accordance with the techniques described herein may help a user program electrical stimulation parameters for electrical stimulation therapy delivered by an electrical stimulator in an efficient manner.

In some examples, a therapeutic window may define bounds for just one electrical stimulation parameter, e.g., amplitude, assuming substantially fixed (e.g., fixed or nearly fixed) levels or ranges for the other electrical stimulation parameters. In other examples, a therapy window may define bounds of values for combinations of electrical stimulation parameters.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator configured to generate and deliver electrical stimulation therapy to one or more regions of brain 28 of patient 12 via one or more electrodes 24, 26 of leads 20A and 20B, respectively.

In the example shown in FIG. 1, therapy system 10 may be referred to as a deep brain stimulation (DBS) system because IMD 16 is configured to deliver electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). For example, in some examples, IMD 16 may provide cortical stimulation therapy to patient 12, e.g., by delivering electrical stimulation to one or more tissue sites in the cortex of brain 28. As another example, IMD 16 may provide vagal nerve stimulation (VNS) therapy to patient 12 by delivering electrical stimulation to one or more vagal nerve tissue sites.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post traumatic stress disorder, dysthymic disorder, and obsessive compulsive disorder (OCD), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

Therapy systems configured for treatment of other patient conditions via delivery of therapy to brain 28 or another suitable target therapy delivery site in patient 12 can also be used in accordance with the techniques for determining one or more therapeutic windows disclosed herein. For example, in other applications of therapy system 10, the target therapy delivery site within patient 12 may be a location proximate to a spinal cord or sacral nerves (e.g., the S2, S3 or S4 sacral nerves) in patient 12 or any other suitable nerve, organ, muscle or muscle group in patient 12, which may be selected based on, for example, a patient condition. For example, therapy system 10 may be used to deliver electrical stimulation or a therapeutic agent to tissue proximate to a pudendal nerve, a perineal nerve or other areas of the nervous system, in which cases, leads 20 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, muscle stimulation, for mitigation of other peripheral and localized pain (e.g., leg pain or back pain).

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment. Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the Circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a stimulation generator of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, and, in the case of electrical stimulation pulses, pulse rate, pulse width, waveform shape, and other appropriate parameters such as duration or duty cycle. In addition, if different electrodes are available for delivery of stimulation, a therapy parameter of a therapy program may be further characterized by an electrode combination, which may define selected electrodes 24, 26 and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

External medical device programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, e.g., a power button, the buttons and the keypad may be soft keys that change in function depending upon the section of the user interface currently viewed by the user, or any combination thereof In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs that may provide efficacious therapy to patient 12 to address symptoms associated with the patient condition. For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Programmer 14 may assist the clinician in the creation/identification of therapy programs by providing a system for identifying potentially beneficial therapy parameter values.

As discussed in further detail below, in some examples, programmer 14 (or another computing device) is configured to determine, for at least one electrode (e.g., for each electrode 24, 26) of therapy system 10, a therapeutic window, and generate and display information regarding the determined therapeutic windows. For example, programmer 14 may generate a display that lists each electrode 24, 26, or a subset of electrodes 24, 26, and, for each electrode, the respective therapeutic window. The therapeutic windows can be displayed as, for example, an efficacy threshold value and an adverse-effects threshold, which may define the boundaries of the therapeutic window in some examples (e.g., X to Y, or X-Y, where X and Y are values for a particular stimulation parameter, such as amplitude). In addition, or instead, the therapeutic windows can be displayed as a magnitude of the difference between the efficacy threshold value and the adverse-effects threshold (e.g., a single number that indicates the difference between the efficacy threshold value and the adverse-effects threshold).

As discussed above, the therapeutic windows of electrodes 24, 26 may provide a basis for comparing the potential benefits of each of the electrodes. For example, an electrode associated with a relatively large therapeutic window may indicate that the electrode will provide more latitude to find efficacious electrical stimulation parameter values for the patient than another electrode associated with a relatively small therapeutic window. In some examples, the therapeutic windows may be determined based on the actual implantation site of leads 20 (e.g., as discussed below with respect to FIGS. 4-6) within patient 12, i.e., post-operatively, such that the information identifying the therapeutic windows for each of the electrodes 24, 26 may be specifically tailored to patient 12. As a result, the therapeutic windows may provide a useful basis for selecting electrode combinations for programming IMD 16.

In some examples, the therapeutic windows may be determined before leads 20 are implanted in patient 12, e.g., pre-operatively. For example, the therapeutic windows may be determined based on the expected implantation site of leads 20 in patient 12. In these examples, the therapeutic windows may be determined based on VTAs determined using images of patient 12 (e.g., based on a brain atlas specific to patient 12), such that the information identifying the therapeutic windows for each of the electrodes 24, 26 may be specifically tailored to patient 12. The target location of leads 20 and electrodes 24, 26 may be selected and modeled, e.g., by a processor of programmer 14, in order to determine the VTAs expected to result from delivery of electrical stimulation by select electrode(s) 24, 26 of leads 20 if leads 20 were implanted in patient 12. In this way, the therapeutic windows may be used to determine at least some electrical stimulation parameter values pre-operatively, prior to implantation of leads 20. In addition, programmer 14 (or another device) may determine the therapeutic windows based on different target locations for electrodes 24, 26, e.g., in order to pre-operatively select an actual implant site for leads 20. Processor 14 may, for example, select the implant site that results in the relatively largest therapeutic windows or the relatively greatest number of electrodes associated with therapeutic windows greater than or equal to a predetermined size.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system for which a therapeutic window may be determined for one or more electrodes 24, 26. The techniques described herein can be used to determine the therapeutic window of one or more electrodes of other therapy systems, such as therapy systems with other configurations of leads and electrodes, therapy systems with more than one IMD, and therapy systems including one or more leadless electrical stimulators (e.g., microstimulators having a smaller form factor than IMD 16 and which may not be coupled to any separate leads). The leadless electrical stimulators can be configured to generate and deliver electrical stimulation therapy to patient 12 via one or more electrodes on an outer housing of the electrical stimulator.

During implantation of lead 16 within patient 12, a clinician may attempt to position electrodes 24, 26 of leads 20 close to or within a target anatomical region. The anatomical region within patient 12 that serves as the target tissue site for stimulation delivered by IMD 14 may be selected based on the patient condition. For example, stimulating particular structures of brain 18, such as the Substantia Nigra, may help reduce the number and magnitude of tremors experienced by patient 12. Other anatomical regions for DBS may include the subthalamic nucleus, globus pallidus interna, ventral intermediate, and zona inserta.

While DBS may successfully reduce symptoms of some neurological diseases, the stimulation may also cause unwanted side effects, also referred to herein as adverse effects. Side effects may include incontinence, tingling, loss of balance, paralysis, slurred speech, loss of memory, loss of inhibition, and many other neurological problems. Side effects may be mild to severe. DBS may cause one or more adverse effects by inadvertently providing electrical stimulation pulses to anatomical regions near the targeted anatomical region. These anatomical regions may be referred to as regions associated with adverse stimulation effects. For this reason, a clinician may program IMD 16 with a therapy program (or a plurality of therapy programs) that defines stimulation parameter values that balance effective therapy and minimize side effects.

With the aid of programmer 14 or another computing device, a clinician may select values for therapy parameters for therapy system 10, including an electrode combination. By selecting particular electrodes 24, 26 for delivering electrical stimulation therapy to patient 12, a clinician may modify the electrical stimulation therapy to target one or more particular regions of tissue (e.g., specific anatomical structures) within brain 28 and avoid other regions of tissue within brain 28. In addition, by selecting values for the other stimulation parameter values that define the electrical stimulation signal, e.g., the amplitude, pulse width, and pulse rate, the clinician may generate an efficacious therapy for patient 12 that is delivered via the selected electrode subset. Due to physiological diversity, condition differences, and inaccuracies in lead placement, the parameter values may vary between patients.

During a programming session, the clinician may determine one or more therapy programs that may provide effective therapy to patient 12. Patient 12 may provide feedback to the clinician as to the efficacy of the specific program being evaluated, which may include information regarding adverse effects of delivery of therapy according to the specific program. Once the clinician has identified one or more programs that may be beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

A therapeutic window of a particular electrode 24, 26 may indicate whether the electrode may be useful for providing efficacious stimulation therapy to patient 12. Thus, information indicating the therapeutic window of electrodes 24, 26 may help aid the selection of one or more electrode combinations that may provide efficacious electrical stimulation therapy to patient 12.

In some existing techniques, a clinician may manually determine the therapeutic window for each electrodes of a therapy system in a unipolar stimulation mode, e.g., during initial programming of the system for a patient. This process may be relatively time consuming. For example, one electrode at a time, the clinician may set the IMD can to be the anode, the electrode to be the cathode, and set the pulse width and frequency of the electrical stimulation to some constant default values. Then, the clinician may systematically increase the amplitude of electrical stimulation in incremental steps to identify the amplitude that first yields some efficacy for the patient. The clinician may then continue increasing the amplitude in incremental steps to identify the amplitude that first yields some undesirable side effects for the patient. The difference between these two amplitudes may be the therapeutic window for the electrode.

While the therapeutic window information determined using this manual technique may be useful, obtaining the therapeutic window information in this manner can be relatively tedious and time-consuming for the clinician and patient. In addition, the manual process of determining the therapeutic window for a plurality of electrodes can fatigue the patient due to the relatively long duration of time required to determine the therapeutic window, the frequent delivery of the electrical stimulation to the patient to determine the therapeutic windows, or both. If the patient is fatigued, the results of the electrical stimulation may be adversely impacted, which may decrease the accuracy of the determined therapeutic windows.

In some examples described herein, a processor of therapy system 10 (e.g., a processor of IMD 16 or programmer 14) is configured to automatically determine the therapeutic windows for electrodes 24, 26 based on a VTA expected to result from electrical stimulation delivered via the respective electrode in a unipolar configuration. In contrast to the manual technique of determining therapeutic windows discussed above, the therapeutic windows are determined using computer modeling, rather than based on the results of actual electrical stimulation delivered to patient 12 by IMD 16 with the selected stimulation parameter values. Thus, in some examples, the processor may determine the therapeutic windows without patient 12 being present in a clinic, which may help reduce the amount of time patient 12 is required to be in the clinic in order to program IMD 16. In addition, in some examples, therapeutic windows may be estimated prior to implanting leads 20 in patient 12, which may provide a starting point for programming electrical stimulation parameters for IMD 16 after implanting leads 20 in patient 12.

An example technique for determining the therapeutic window for each electrode 24, 26 of system 10 is described in further detail below with respect to FIGS. 4, 7, and 8. For ease of description, the techniques are primarily described as being employed by programmer 14. In other examples, the techniques may be implemented by any suitable device, such as IMD 16 or another computing device (e.g., a remote computing device such as a cloud computing device), alone or in combination with programmer 14.

As described in further detail below, in some examples, programmer 14 determines the therapeutic window for each electrode 24, 26 based on a volume of tissue expected to be activated by electrical stimulation delivered via the respective electrode and a set of electrical stimulation parameter values. Programmer 14 may be configured to generate the VTA for a particular electrode and a set of electrical stimulation parameter values using any suitable technique, such as any one of the techniques described below with respect to FIG. 6. In some examples, a processor of programmer 14 automatically determines the therapeutic window for a particular electrode by at least determining an efficacy threshold based on the VTA expected to result from the delivery of electrical stimulation according to a set of electrical stimulation parameter values including the stimulation parameter at the efficacy threshold, and determining the adverse-effects threshold based on the VTA expected to result from the delivery of electrical stimulation according to a set of electrical stimulation parameter values including the stimulation parameter at the adverse-effects threshold. The therapeutic window is defined between the efficacy threshold and the adverse-effects threshold.

For example, the processor may determine a VTA expected to result from electrical stimulation delivered by a selected electrode (in a unipolar configuration) according to an initial set of electrical stimulation parameters. The processor may then adjust the value (e.g., by increasing or decreasing the value) of at least one electrical stimulation parameter of the set (e.g., one or more of the amplitude, the frequency, the pulse width, and the like) in order to determine the efficacy threshold and the adverse-effects threshold. For example, the processor may incrementally increase the value of an electrical stimulation parameter until the resulting VTA overlaps with one or more efficacy regions of the patient, the efficacy regions being associated with efficacious electrical stimulation. The lowest value at which the resulting VTA overlaps with the one or more efficacy regions may be the efficacy threshold. In addition, the processor may determine the resulting VTA overlaps with one or more efficacy regions of the patient in response to determining the VTA overlaps with the one or more efficacy regions in an amount sufficient to cause one or more efficacious effects of electrical stimulation.

In this example, the processor may also determine the lowest value of the electrical stimulation parameter at which the resulting VTA overlaps with one or more adverse-effects regions of the patient, the second regions being associated with adverse effects of electrical stimulation. The lowest value of the electrical stimulation parameter at which the resulting VTA overlaps with the one or more adverse-effects regions may be the adverse-effects threshold. Again, the processor may determine the resulting VTA overlaps with one or more adverse-effects regions of the patient in response to determining the VTA overlaps with the one or more adverse-effects regions in an amount sufficient to cause one or more adverse effects of electrical stimulation. In addition, by determining which adverse-effects regions of tissue the VTA overlap with, the processor may also be able to determine which side effects may result from the delivery of electrical stimulation via the electrode.

The electrical stimulation parameter value at which the VTA overlaps with the one or more adverse-effects regions may be higher than the lowest electrical stimulation parameter value at which a VTA overlaps with the one or more efficacy regions. The processor may then determine the therapeutic window based on the efficacy threshold and the adverse-effects threshold, e.g., the processor may define the therapeutic window as being bounded by the efficacy threshold and the adverse-effects threshold or as having a magnitude substantially equal (e.g., equal or nearly equal) to the difference between the efficacy threshold and the adverse-effects threshold.

In other examples, depending on the electrical stimulation parameter with which the therapeutic window is defined, the highest value at which the resulting VTA overlaps with the one or more efficacy regions may be the efficacy threshold and the highest value of the electrical stimulation parameter at which the resulting VTA overlaps with the one or more adverse-effects regions may be the adverse-effects threshold. In these examples, the electrical stimulation parameter value at which the VTA overlaps with the one or more adverse-effects regions may be lower than the lowest electrical stimulation parameter value at which a VTA overlaps with the one or more efficacy regions.

After determining the therapeutic windows for each electrode 24, 26, the processor of programmer 14 may store the therapeutic windows with an indication of the associated electrode, generate and present a display that includes a list of a plurality of electrodes and respective therapeutic windows, or any combination thereof.

Figure 2:
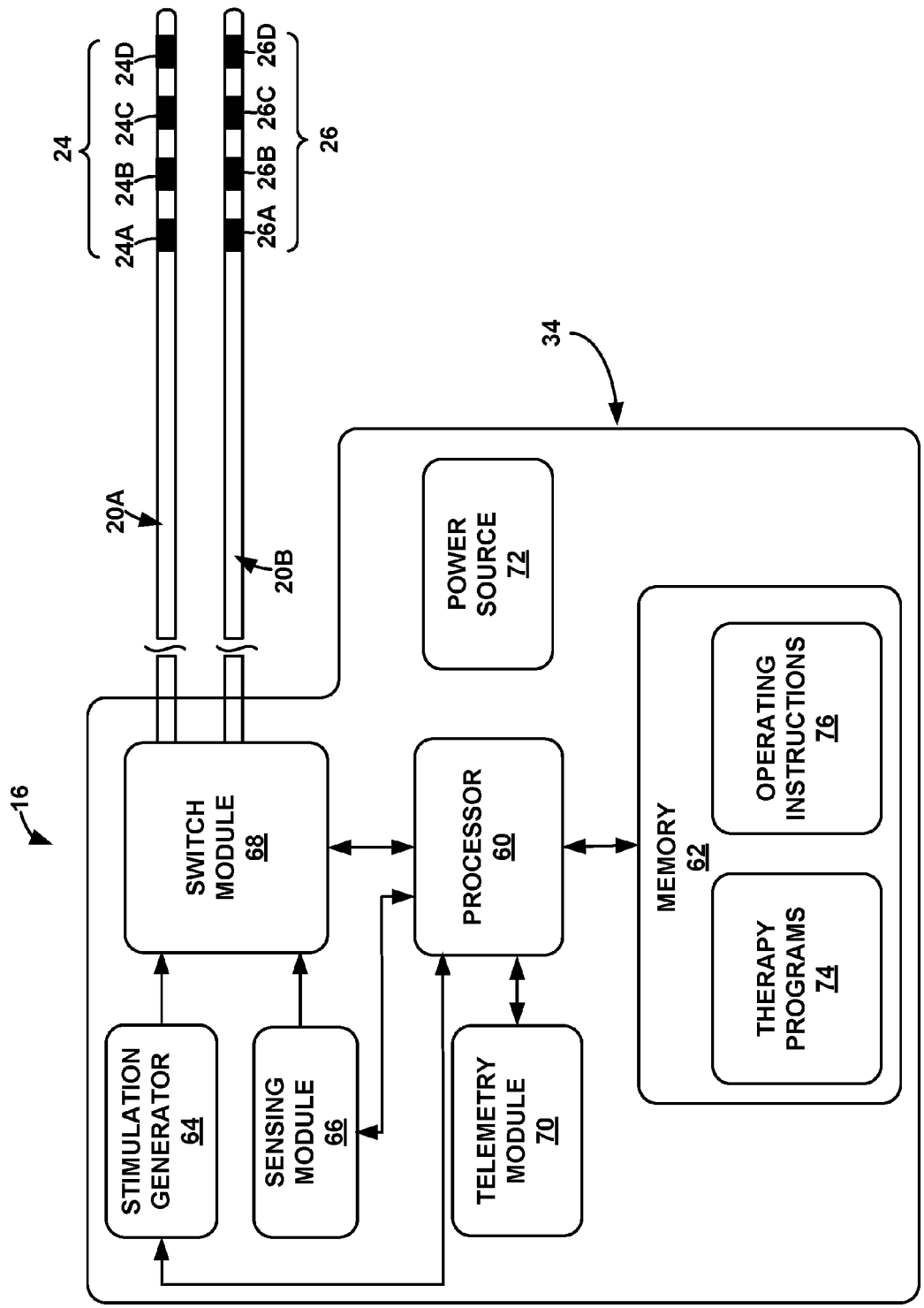
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74 and operating instructions 76, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. Each stored therapy program 74 may also be referred to as a set of therapy parameter values. Operating instructions 76 guide general operation of IMD 16 under control of processor 60, and may include instructions for monitoring brain signals within one or more brain regions via electrodes 24, 26 and delivering electrical stimulation therapy to patient 12.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
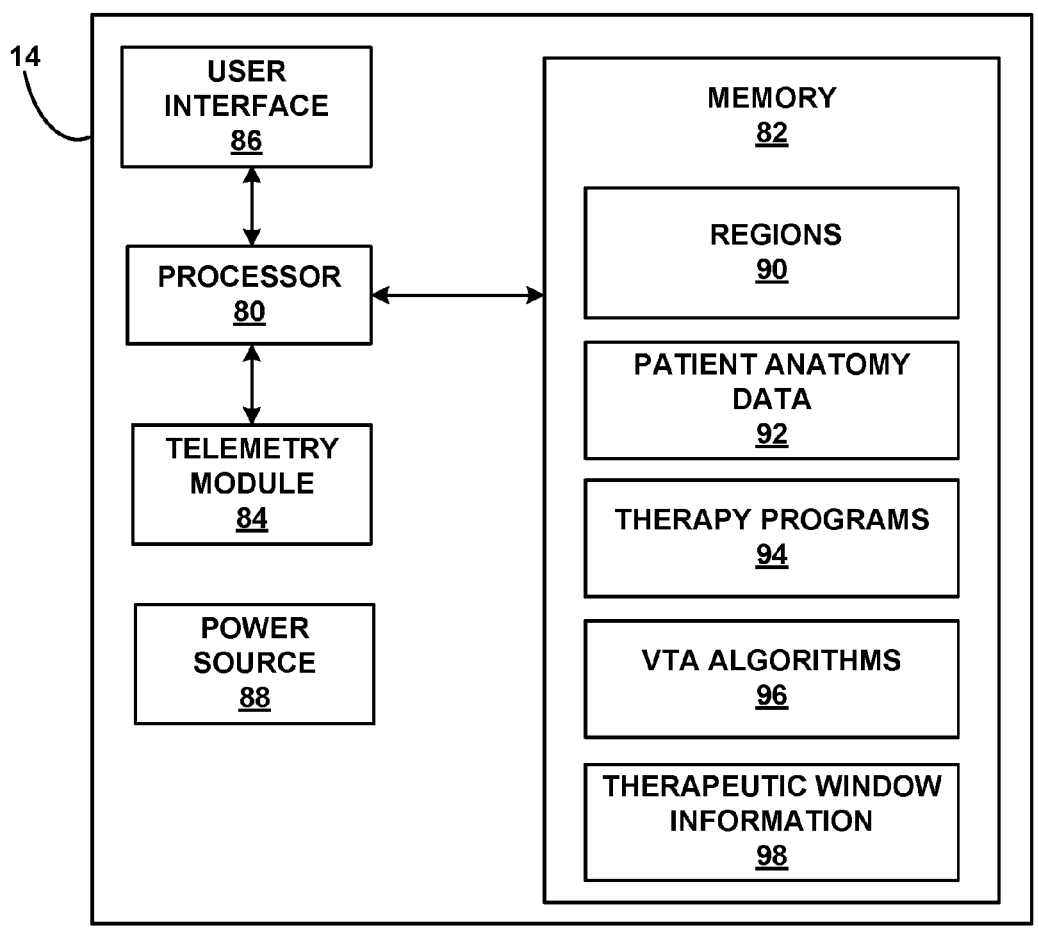
FIG. 3 is a functional block diagram illustrating components of an example medical device programmer.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, with which processor 80 may present information related to the therapy (e.g., electrodes and associated therapeutic windows). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate though user interfaces presented by processor 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores regions 90, patient anatomy data 92, therapy programs 94, VTA algorithms 96, and therapeutic window information 98.

Regions 90 stores information identifying one or more regions of tissue of brain 28 (or another part of the body of the patient) associated with efficacious therapy delivery. These regions may be referred to as efficacy regions. Regions 90 also stores information identifying one or more regions of tissue of brain 28 (or another part of the body of patient) associated with adverse stimulation effects. These regions may be referred to as adverse-effects regions. The regions 90 may be identified using any suitable convention. In some examples, the efficacy and adverse-effects regions are identified by specific brain structures or parts of brain structures, coordinates of any suitable coordinate system to which leads 20 and brain 28 are registered, other anatomical structures, pixels of a two-dimensional (2D) grid to which brain 28 or another portion of the body of patient 12 is registered, voxels of a three-dimensional (3D) grid to which brain 28 or another portion of the body of patient 12 is registered (as discussed in further detail below), or any combination thereof.

The efficacy regions and adverse-effects regions stored by regions 90 may differ depending on the patient condition. For example, if therapy system 10 is implemented to manage tremors experienced by patient 12, regions 90 may include the substantia nigra because for some patients, stimulating the substantia nigra, may help reduce the number and magnitude of tremors experienced by the patient.

In some examples, a clinician selects the stored regions 90. In other examples, the regions 90 are preselected and associated with a patient condition; processor 80 or a clinician may determine the regions 90 relevant to patient 12 by selecting the patient condition for which system 10 is implemented to manage.

Processor 80 is configured to generate a VTA for a particular set of stimulation parameter values, where the VTA represents the volume of tissue of patient 12 expected to be activated by the delivery, by a particular electrode (or combination of electrodes), of electrical stimulation to tissue of patient 12 according to the set of stimulation parameters. Processor 80 is configured to generate, for a particular electrode and a set of electrical stimulation parameter values, a VTA using VTA algorithms 96 and patient anatomy data 92 stored by memory 82 to generate the VTA. Patient anatomy data 92 may, for example, include the location of implanted electrodes 24, 26 in brain 28, the anatomical structure of patient 12, and the characteristics of the tissue, such as the impedance, proximate to implanted electrodes 24, 26. In examples in which the therapeutic windows (or just the efficacy and adverse-effects thresholds) are determined before leads 20 are implanted in patient 12, patient anatomy data 92 may not include the actual location of implanted electrodes 24, 26 in brain 28, but, rather, a target location for electrodes 24, 26 in brain 28. Patient anatomy data 92 may be created from any type of imaging modality, such as, but not limited to, computed tomography (CT), magnetic resonance imaging (MM), x-ray, fluoroscopy, and the like.

VTA algorithms 96 may include one or more algorithms that processor 80 may implement to generate a VTA for a particular set of electrical stimulation parameter values and one or more active electrodes. When IMD 16 delivers electrical stimulation to tissue of patient 12 via an electrode (or combination of electrodes), an electrical field propagates away from the electrode. Processor 80 can implement the algorithms 96 to estimate which neurons will be activated by the electrical field propagating away from an electrode 24, 26 during the delivery of electrical stimulation by the electrode.

In some examples, the VTA algorithms 96 may include, for example, electrical field model equations that define how an electrical field propagates away from an origin location. In addition, VTA algorithms 96 may also include a set of equations, a lookup table, or another type of model that defines threshold action potentials of particular neurons that make up the anatomical structure, as defined by the patient anatomy data, affected by an electrical field. If the voltage or current amplitude of the electrical field is above the threshold action potential of any neuron within the electrical field, that neuron will be activated, e.g., cause a nerve impulse. Due to changes in electrical current propagation and threshold action potentials (e.g., a threshold voltage) required to activate a neuron, the activation of neurons may vary with the location of tissue around the lead. Some neurons may activate further from the lead with smaller voltages while other neurons may only be activated close to the lead because of a high voltage threshold.

In some examples, memory 82 also stores information regarding the hardware characteristics of leads 20 and processor 80 generates the VTA based on the hardware characteristics. The hardware characteristics may include, for example, the number or types of leads 20 implanted within patient 12, the number of electrodes 24, 26, the size of each of the electrodes 324, 26, the type of electrodes 24, 26 (e.g., ring electrodes, partial-ring electrodes, segmented electrodes), and the like.

In some examples, processor 80 is configured to store determined therapeutic windows and associated electrodes in memory 82 as therapeutic window information 98. A clinician may review the stored information 98, e.g., during programming of IMD 16 to select one or more electrode combinations with which IMD 16 may deliver efficacious electrical stimulation to patient 12. For example, the clinician may interact with user interface 86 to retrieve the stored therapeutic window information 96. In some examples, processor 80 is configured to generate and display a graphical user interface that indicates, for at least one electrode 24, 26 (e.g., each electrode 24, 26 or at least two electrodes 24, 26), the respective therapeutic window. The clinician may then ascertain, relatively quickly, from the displayed information which electrodes have the largest therapeutic window, which may be the electrodes associated with the most latitude to find electrical stimulation parameter values that provide efficacious electrical stimulation therapy for patient 12.

In some examples, the clinician (or another user) may provide input via user interface 86 to manipulate the therapeutic window information. For example, in response to receiving user input requesting the list of electrodes be ordered by therapeutic window, efficacy threshold, or adverse-effects threshold, processor 80 may reorganize the list of electrodes based on the size of the associated therapeutic window, efficacy threshold, or adverse-effects threshold, respectively (e.g., from large to small or vice versa).

Processor 80 may be configured to generate other types of interfaces. For example, processor 80 may be configured to generate a display including a list of electrodes (e.g., each electrode may be assigned a unique alphanumeric identifier or a graphical identifier) ordered based on the associated therapeutic windows, efficacy thresholds, or adverse-effects threshold without displaying the therapeutic windows, efficacy thresholds, or adverse-effects threshold, respectively. The clinician may then provide input via user interface 86 requesting additional information about a particular electrode. In response to receiving the user input, processor 80 may present another user interface with further details about the selected electrode, such as the one or more of the associated therapeutic window, efficacy threshold, or adverse-effects threshold.

In some examples, patient 12, a clinician or another user may interact with user interface 86 of programmer 14 in other ways to manually select therapy programs, generate new therapy programs, modify therapy programs, transmit the new programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

Figure 4:
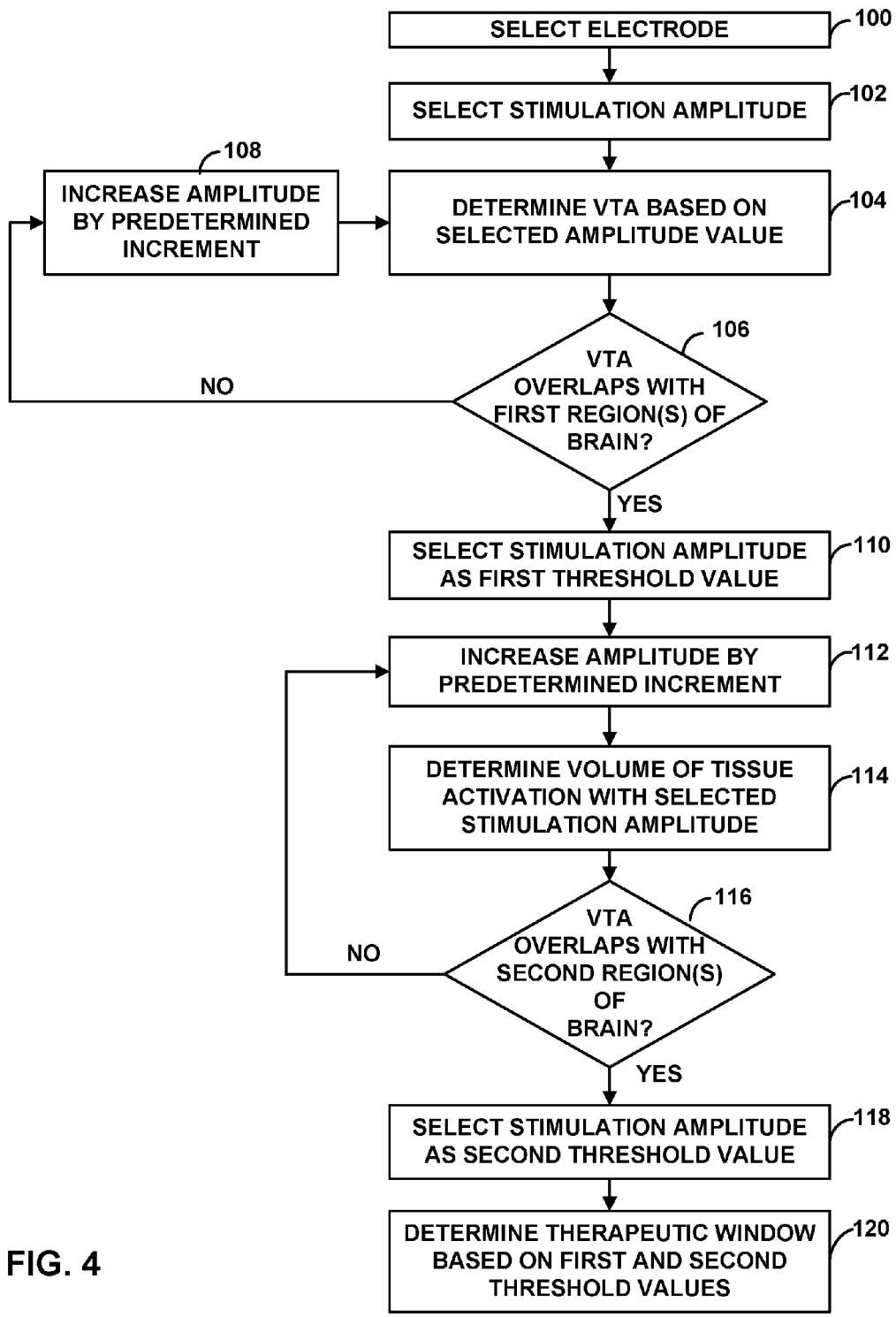
FIG. 4 is a flow diagram illustrating an example technique for determining a therapeutic window for at least one electrode of a therapy system

FIG. 4 is a flow diagram illustrating an example technique for determining a therapeutic window for at least one electrode of a therapy system. While the techniques shown in FIGS. 4-8 are primarily described as being performed by processor 80 of programmer 14, in other examples, a processor of another device, such as processor 60 of IMD 16, can perform any part of the techniques shown in FIGS. 4-8, alone or in combination with processor 80. In addition, while the techniques shown in FIGS. 4, 7, and 8 are described with respect to determining the therapeutic window for each electrode 24, 26 of a plurality of electrodes 24, 26 of system 10, in other examples, the techniques shown in FIGS. 4, 7, and 8 can be used to determine the therapeutic window for any number of electrodes, such as only one electrode, only a subset of electrodes of system 10, or all of the electrodes of system 10.

A therapeutic window may be specifically associated with a single electrode or a subset of electrodes (e.g., a specific electrode combination) because the efficacy threshold and adverse-effects threshold depends upon the results (or expected results) of the electrical stimulation delivered by IMD 16 with the electrode or subset of electrodes. In the example technique shown in FIG. 4 (as well as FIGS. 7 and 8), processor 80 determines the therapeutic window for an electrode based on a VTA resulting from electrical stimulation delivered via the electrode in a unipolar configuration, e.g., using the housing of IMD 16 as a reference. In other examples, processor 80 may, according to the techniques shown in FIGS. 4, 7, and 8, determine the therapeutic window for an electrode combination (e.g., for bipolar electrical stimulation).

In the technique shown in FIG. 4, processor 80 selects an electrode (100) for which a therapeutic window will be determined. Processor 80 may select the electrode from a plurality of electrodes 24, 26.

A therapeutic window may be defined by a range of values of any suitable electrical stimulation parameter that may affect the results (both therapeutic and adverse) of electrical stimulation delivered by IMD 16. In the example shown in FIG. 4, the therapeutic window determined by processor 80 is defined by a range of stimulation amplitude values (also referred to herein as "amplitude" values). The amplitude values indicate the amplitude of the electrical stimulation signal delivered by IMD 16, and may be voltage amplitude values or current amplitude values, e.g., depending on whether IMD 16 is a voltage controlled device or a current controlled device. In other examples, however, the therapeutic window may be defined by another type of electrical stimulation parameter, such as, but not limited to, a frequency or pulse width.

Processor 80 may select an initial amplitude value (102). In some examples, memory 82 of programmer 14 stores a predetermined maximum amplitude value (or other stimulation parameter value), and processor 80 selects the initial amplitude value to be less than the predetermined maximum. The predetermined maximum can be, for example, a stimulation amplitude value that is known to be higher than an expected efficacy threshold value. The initial amplitude value may be a part of an initial set of electrical stimulation parameter values that processor 80 selects in order to start the determination of the therapeutic window for an electrode. In some examples, the initial set of electrical stimulation parameter values includes values for a pulse width, a frequency, and an amplitude of electrical stimulation. The pulse width and frequency may remain fixed at the values of the initial set of electrical stimulation parameter values, while processor 80 may adjust the amplitude from the initial amplitude value in order to determine the therapeutic window. The initial amplitude value can be one that is expected (e.g., based on past clinician experience or based on computer modeling) to be less than the efficacy threshold for patient 12 when electrical stimulation is delivered via the selected electrode. The efficacy threshold may be the lowest amplitude value at which efficacious results of electrical stimulation may be observed.

If processor 80 determines the therapeutic window for a plurality of electrodes, processor 80 may start each therapeutic window determination with the initial set of electrical stimulation parameter values, or at least with substantially the same (e.g., the same or nearly the same) values of the electrical stimulation parameters that remain fixed during the therapeutic window determination. In this way, the values of the electrical stimulation parameters that remain fixed during the therapeutic window determination are substantially the same for all the electrodes, which may help aid the comparison of the therapeutic windows to each other.

Processor 80 determines the VTA based on the selected amplitude value (104), where the VTA indicates the volume of tissue that is expected (e.g., estimated) to be activated by the stimulation field resulting from delivery of electrical stimulation by IMD 16 via the selected electrode (in a unipolar configuration), the electrical stimulation being generated by IMD 16 in accordance with the selected stimulation amplitude value and the other stimulation parameter values of the initial set. Processor 80 can determine the VTA using any suitable technique, such as the example technique described with respect to FIG. 6. As described with respect to FIG. 6, in some examples, processor 80 utilizes an algorithm (e.g., stored as a VTA algorithm 96 in memory 82 of programmer 14) to determine an electrical field that indicates the stimulation field that will propagate away from the electrode when a signal stimulation signal initial set of stimulation parameter values is delivered by the electrode. Based on the electrical field and patient anatomy data 92 (e.g., one or more impedance characteristics of patient neural tissue proximate the selected electrode), processor 80 may estimate the volume of tissue of brain 28 (or other tissue areas) that will be activated by the electrical field.

Example techniques that processor 80 may use to determine a VTA (104) are described in commonly-assigned U.S. Pat. No. 7,822,483 to Stone et al., entitled, "ELECTRICAL AND ACTIVATION FIELD MODELS FOR CONFIGURING STIMULATION THERAPY" and issued on Oct. 26, 2010, and commonly-assigned U.S. Patent Application Publication No. 2013/0289380 by Molnar et al., entitled, "VISUALIZING TISSUE ACTIVATED BY ELECTRICAL STIMULATION," and filed on Mar. 14, 2013. The entire content of U.S. Pat. No. 7,822,483 to Stone et al. and U.S. Patent Application Publication No. 2013/0289380 by Molnar et al. is hereby incorporated by reference.

In accordance with some examples described in U.S. Patent Application Publication No. 2013/0289380 by Molnar et al., a volume of activation of tissue resulting from delivery of electrical stimulation according to a set of stimulation parameter values may be determined based on a uniform or non-uniform grid of neuron representatives that indicate the neurons of the tissue of the patient proximate electrodes 24, 26. Each neuron representative may be associated with a threshold value of activation (also referred to herein as an "activation threshold value" or "activation threshold"). The threshold value for each neuron representative may be obtained using a binary search algorithm. The threshold value is a stimulation voltage or current amplitude, that when applied to an actual neuron of the type being modeled by processor 80, results in a propagating action potential along the neuron. In some examples, the action potential is considered to have excited, or "activated," the neuron representative if the transmembrane potential reached a threshold greater than 0 mV. As used herein, the threshold value of activation may be referred to as a threshold, an activation threshold, or a propagation threshold.

After generating the VTA (104), processor 80 determines whether the VTA overlaps with one or more first regions of tissue (106). In the example shown in FIG. 4, the one or more first regions of tissue are efficacy regions of brain 28, which is a region of brain tissue associated with efficacious therapy delivery when the tissue (e.g., a sufficient amount of tissue) in the region is activated. As discussed above with respect to FIG. 3, in some examples, information defining or otherwise identifying the first region may be stored in memory 82 of programmer 14, as part of regions 90.

Processor 80 can determine whether the VTA overlaps with the one or more first regions of tissue (106) using any suitable technique. In some examples, processor 80 determines whether the coordinates of the perimeter of the VTA overlap with the coordinates of the one or more first regions, the coordinates being stored by memory 82. In addition, or instead, if one or more first regions are defined by an anatomical structure of brain 28, processor 80 may determine whether the coordinates of the perimeter of the VTA fall within the anatomical structure in order to determine whether the VTA overlaps with the one or more first regions. In another example, processor 80 determines whether the VTA overlaps with the one or more first regions of tissue (106) using the technique described with respect to FIG. 5, in which processor 80 registers the VTA and one or more first regions to a 3D grid of voxels, and determines the overlap based on the voxels lying in both the VTA and the one or more first regions.

In response to determining the VTA does not overlap with the one or more first regions ("NO" branch of block 106), processor 80 increases the amplitude by a predetermined increment (108), and then determines the VTA resulting from the modified amplitude (104). The predetermined increment may be stored by memory 82 of programmer 14 (or a memory of another device). The predetermined increment may be selected using any suitable criteria. In some examples, the size of the increment by which the stimulation amplitude (or other parameter) is adjusted may be selected to be large enough to result in a change to the VTA, but small enough to provide a gradual change in size to the VTA. For example, the size of the increment by which processor 80 may adjust the stimulation amplitude may be 0.1 millivolts, 0.2 millivolts, 0.3 millivolts, 0.4 millivolts, or 0.5 millivolts, although other increments can be used in other examples. The gradual change may enable processor 80 to modify the size of the VTA to be adjusted with small enough granularity to enable a relatively accurate determination of the boundaries of the therapeutic window.

Processor 80 may continue increasing the amplitude by the predetermined increment (108) and determining the VTA (104) until the determined VTA overlaps with the one or more first regions of brain 28 ("YES" branch of block 106). In response to determining the VTA generated based on a particular stimulation amplitude value overlaps with the one or more first regions of brain 28 ("YES" branch of block 106), processor 80 selects the amplitude value as the first threshold value (110). In examples in which the one or more first regions are associated with efficacious results of electrical stimulation, the first threshold value may be an efficacy threshold for the selected electrode.

Processor 80 may continue increasing the amplitude by a predetermined increment (relative to the first threshold value) (112) and determining the VTA based on the amplitude value (114) until processor 80 determines the VTA overlaps with one or more second regions of tissue ("YES" branch of block 116). The predetermined increment with which the amplitude is increased from the first threshold value may be the same as, or different than, the predetermined increment with which processor 80 increased the amplitude (108) in order to determine the first threshold value.

The one or more second regions may each be a region of tissue of patient 12 associated with adverse stimulation effects. In the example shown in FIG. 4, one or more second regions are regions of brain 28. As with the one or more first regions, information defining or otherwise identifying the one or more second regions may be stored by memory 82 (FIG. 3) of programmer 14, as part of region 90.

Processor 80 may determine whether the VTA overlaps with one or more second regions of brain 28 (116) using any suitable technique, such as any of those described above with respect to determining whether a VTA overlaps with the one or more first regions (106). In response to determining the VTA generated based on a particular stimulation amplitude value overlaps with the one or more second regions of brain 28 ("YES" branch of block 116), processor 80 selects the amplitude value as the second threshold value (118). In examples in which the one or more second regions are associated with adverse effects of electrical stimulation, the second threshold value may be an adverse-effects threshold for the selected electrode.

Processor 80 determines the therapeutic window for the electrode based on the determined first and second threshold values (120). In some examples, the therapeutic window is bounded by the first and second threshold values. The therapeutic window may include the first threshold value, but not the second threshold value in some examples. In some examples, processor 80 may associate the determined therapeutic window with the electrode and store the electrode and associated therapeutic window in memory 82 of programmer 14 or a memory of another device. In addition, in some examples, processor 80 may store, in memory 82, the first threshold as a predicted efficacy threshold for patient 12 and the second threshold as an adverse-effects threshold for patient 12, and associate the efficacy and adverse-effects thresholds with the electrode in memory 82.

Using the technique shown in FIG. 4, processor 80 may determine the efficacy threshold and adverse-effects threshold and the therapeutic window for each electrode of a plurality of electrodes based on an expected effect of the electrical stimulation, and in the absence of the actual delivery of electrical stimulation to patient 12 via the electrodes, as in the manual technique described above. As a result, a clinician may, using programmer 14, determine the efficacy and adverse-effects thresholds and the therapeutic windows for the electrodes 24, 26 of leads 20 (or just a subset of electrodes 24, 26) in advance of a programming session with patient 12. This may help reduce the amount of time patient 12 is in the clinic to program efficacious therapy programs for IMD 16.

The clinician may, in some examples, confirm one or more of the efficacy and adverse-effects thresholds and the therapeutic windows automatically determined by processor 80. For example, the clinician may, using programmer 14 or another device, control IMD 16 to deliver electrical stimulation to patient 12 via a selected electrode with a set of electrical stimulation parameter values, and then increase the amplitude value while maintaining the other electrical stimulation parameters at relatively constant values. The clinician may then determine, based on patient input or based on the input of one or more sensors that indicates the effects of electrical stimulation, a first amplitude value at which therapeutic effects of stimulation were first observed, and a second amplitude value at which adverse effects of stimulation were first observed. Processor 80, or the clinician, may compare the first amplitude value to the efficacy threshold associated with the selected electrode in memory 82 and compare the second amplitude value to the adverse-effects threshold associated with the selected electrode. In response to determining the first amplitude value and the efficacy threshold are substantially the same (e.g., differ by no more than the amount of the predetermined increment used by the processor 80), processor 80 may confirm the efficacy threshold. In response to determining the second amplitude value and the adverse-effects threshold are substantially the same (e.g., differ by no more than the amount of the predetermined increment 108 used by the processor 80), processor 80 may confirm the adverse-effects threshold.

In the technique shown in FIG. 4, whether or not the value of a selected stimulation parameter value is increased or decreased in order to determine the first and second threshold values may depend on whether the first or second threshold values are determined first, the type of stimulation parameter used to define the thresholds, or any combination thereof. For example, in other examples of the technique shown in FIG. 4, instead increasing the amplitude (108, 112) to determine the first and second threshold values, processor 80 may select a relatively high stimulation amplitude value (102) and decrease the amplitude in predetermined increments in order determine the first and second threshold values. In these examples, processor 80 may determine the second threshold prior to determining the second threshold.

While FIG. 4 illustrates a technique in which processor 80 determines the therapeutic window for a selected electrode by modifying the value of only one electrical stimulation parameter value and holding the other electrical stimulation parameter values constant, in other examples, processor 80 may determine the therapeutic window for a selected electrode by modifying the value of more than one electrical stimulation parameter value. In these examples, the therapeutic window may be defined by multiple electrical stimulation parameters.

Processor 80 may determine whether a VTA sufficiently overlaps with one or more particular regions of brain 28 (106, 116) or another region of tissue within patient 12 using any suitable technique. The overlapping portions of a VTA and the one or more regions of space may cover the same space (e.g., a volume). In some examples, processor 80 may determine there is overlap between a VTA and the first or second regions in response to determining the amount of commonality in 3D space between the VTA and respective region of tissue may be sufficient to produce an efficacious result or an adverse result, respectively. Processor 80 may use the technique shown in FIG. 5 to assess the amount of commonality in 3D space between the VTA and respective region of tissue. In some examples, the commonality of space that constitutes an overlap differs depending on whether processor 80 is determining the efficacy threshold or the adverse-effects threshold. In other examples, the commonality of space that constitutes an overlap is the same for the purposes of determining both the efficacy threshold and the adverse-effects threshold.

Figure 5:
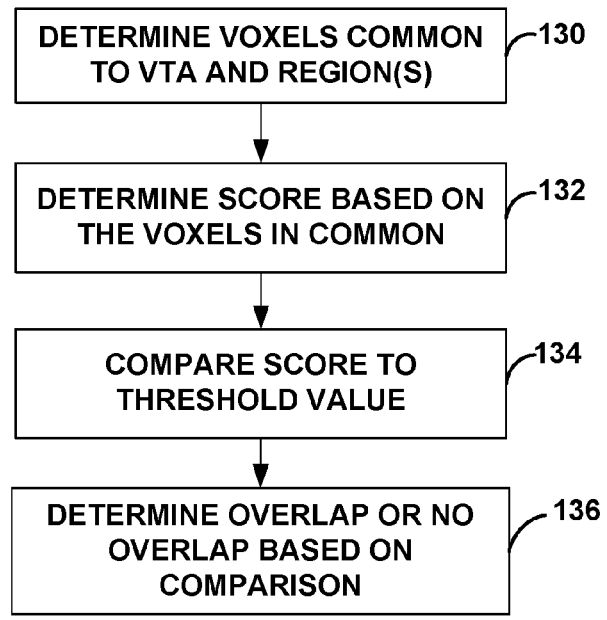
FIG. 5 is a flow diagram illustrating an example technique for determining whether a volume of tissue activation overlaps with a particular region of tissue.

FIG. 5 is a flow diagram of an example technique that processor 80 may implement in order to determine whether a VTA overlaps with one or more particular regions of tissue. The technique shown in FIG. 5 may also be used to determine whether a VTA overlaps with one or more regions of tissue outside of brain 28, such as one or more regions of tissue proximate one or more nerves.

In some examples, processor 80 registers the VTA and the region of brain 28 to each other, such that the VTA and the region are properly positioned and sized relative to each other in 3D space. In the example shown in FIG. 5, processor 80 registers the VTA to a 3D grid of voxels, which are units of volume and a region of tissue is defined by specific voxels of the 3D grid. A voxel is a volume element with which the 3D grid may be constructed. Every point within the space represented by the 3D grid is within one and only one voxel, such that the space is filled by non-overlapping voxels. The voxels of the 3D grid may be substantially the same size in some examples, but can be different sizes in other examples. The voxels of the 3D grid may have any suitable size. While a relatively small size may be useful for fine tuning the determination of both the efficacy and adverse-effects threshold, a relatively small size voxel may also increase the processing time consumed by processor 80 to determine whether a VTA overlaps with one or more particular regions of tissue of patient 12. In some examples, each voxel of the 3D grid is about one cubic millimeter ($mm^3$).

Processor 80 may register the VTA to a 3D grid using any suitable technique, such as by registering the VTA to the 3D grid based on the known locations of leads 20 in brain 28, based on known locations of one or more anatomical structures of brain 28, or both. Other registration techniques may also be used. For example, the VTA may be computed with 3D coordinates relative to the locations of electrodes 24 or 26 of leads 20 and then translated and rotated in three dimensions to coordinates relative to the anatomical structures of the brain 28 based on knowledge of the location of the lead 20 in brain 28.

Figure 6:
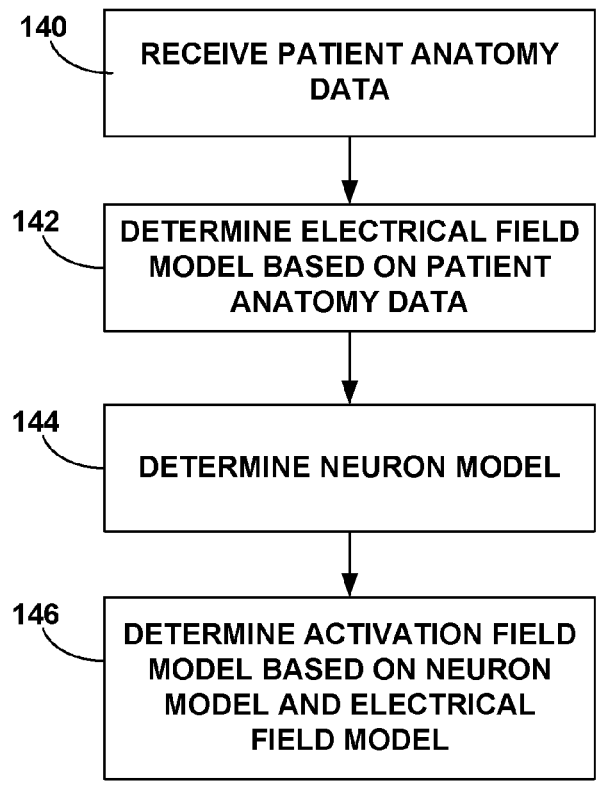
FIG. 6 is a flow diagram illustrating an example technique for determining a volume of tissue activation.

After determining the VTA, e.g., using the technique described with respect to FIG. 6, processor 80 determines the voxels common to the VTA and the one or more regions of tissue (e.g., the first regions or the second regions discussed above with respect to FIG. 4) (130). For example, processor 80 may determine the voxels of the 3D grid that sit within both the VTA and the one or more regions of tissue in order to determine the voxels common to the VTA and the one or more region of tissue. For this determination, for example, processor 80 may determine a voxel of the 3D grid to be within or not within the VTA, and within or not within a region of tissue, based on whether the coordinates of the centroid of the voxel are within the VTA or within the region of tissue, respectively. The centroid of the voxel is that point in space that is the geometric center of the voxel, e.g., as defined in mathematics for convex n-dimensional polyhedra.

A voxel may only be common to the VTA and one region of tissue. Thus, if processor 80 is determining whether there is overlap between the VTA and multiple regions of tissue, processor 80 may, in some examples, determine the voxels common to the VTA and at least one of the regions of tissue.

Processor 80 determines a score based on the voxels in common (132). The score may represent the extent to which the VTA extends within the one or more regions of tissue and, in some examples, may also represent whether the VTA overlaps with the one or more regions of tissue in a manner that may physiologically affect patient 12. For example, in the case of one or more efficacy regions, the score may indicate whether the extent to which the VTA extends within the one or more efficacy regions will result in efficacious therapy delivery to patient 12. In the case of one or more adverse-effects regions, the score may indicate whether the extent to which the VTA extends within the one or more adverse-effects regions will result in one or more adverse effects.

In some examples in which a region of tissue is defined by a plurality of voxels of a 3D grid and processor 80 registers the VTA to the 3D grid, each voxel of the 3D grid may be assigned a value. In these examples, processor 80 may determine the score (132) based on a sum of the values assigned to each voxel common to the VTA and the region of tissue. If processor 80 is determining whether there is overlap between the VTA and multiple regions of tissue, processor 80 may, in some examples, combine the values of the voxels common to the VTA and at least one of the regions of tissue. In this way, the multiple regions can be treated as a single region, even if the multiple regions are not directly adjacent to each other in patient 12. The voxel values may be determined by processor 80 of programmer 14 or a processor of another device prior to the determination of the therapeutic window. In some examples, 3D grid and voxel values may be stored by memory 82 of programmer 14 or a memory of another device.

The value of a particular voxel may change based on the patient condition. For example, for one patient condition, a particular voxel may be associated with a relatively high value, while for another patient condition, the same voxel may be associated with a relatively low value. In some examples, processor 80 selects the 3D grid from memory 82 (FIG. 3) or a memory of another device based on a patient condition of patient 12 for which system 10 is implemented to treat. In other examples, memory 82 only stores the 3D grid relevant to the patient condition for which system 10 is implemented to treat and processor 80 retrieves the 3D grid from memory 82 without having to select the grid from a plurality of grids based on the patient condition. In either example, the values of the voxels may be specific to a patient condition.

The voxel values may be determined based on neuroscience principles, or derived from the cumulative past experience with other patients who have received the same type of therapy. For example, processor 80 (or a processor of another device) may assign each voxel a value based on knowledge that activation of tissue within the particular voxel resulted in efficacious electrical stimulation to patient 12 or a group of patients having the same or similar patient conditions, where the group may or may not include patient 12. As an example, if electrical stimulation of a particular structure within brain 28 (e.g., the subthalamic nucleus) is known to provide therapeutic benefits to a patient having a particular patient condition, processor 80 may assign each voxel within the particular structure a relatively high value (e.g., a 3 on a scale of 0-3).

In the case of Parkinson's disease, for example, electrical stimulation of the subthalamic nucleus may provide efficacious results. Thus, processor 80 may assign each voxel with a centroid that sits within the subthalamic nucleus a relatively high value (e.g., a 3 on a scale of 0-3). In another example, processor 80 may assign each voxel with a centroid that sits within the border between the subthalamic nucleus and adjacent structures a lower value (e.g., a 2 on a scale of 0-3) than the values assigned to the voxels that are more internal to the subthalamic nucleus. This convention may also be used with other regions of tissue. In other examples, processor 80 may assign voxels that are at the border of a brain region such as the subthalamic nucleus, a value that is a percentage of the value of voxels that are 100 percent within the region, corresponding to the percentage of the volume of the voxels that are within the region times the value for voxels that are 100 percent within the region.

As another example, electrical stimulation of the anterior limb of the internal capsule and the thalamus may be associated with adverse effects of electrical stimulation (e.g., muscle contractions or paresthesia in the face). Thus, processor 80 may assign each voxel that sits within the anterior limb of the internal capsule and the thalamus a relatively low value (e.g., a 0 on a scale of 0-3, or, in some examples, a negative value on a scale from −3 to 0, in which 0 is the highest value). The negative scoring system may be used to help differentiate between the regions associated with therapeutic effects of stimulation and the regions associated with adverse effects. Other techniques for assigning each voxel a value may be used.

The voxels within a particular structure within brain 28 or other tissue site may have different values, depending on, for example, the proximity of the portion of the structure or other tissue site represented by the voxel to regions of tissue associated with efficacious electrical stimulation therapy and to regions of tissue associated with adverse effects of electrical stimulation. If, for example, a voxel is close to a region of tissue associated with adverse effects, but is still in a region associated with efficacious therapy delivery, the voxel may be assigned a lower value than if the voxel was further from the region of tissue associated with adverse effects. As discussed below, the voxel values may be updated periodically based on information regarding the efficacy and adverse effects of electrical stimulation therapy.

In order to determine whether the VTA and the one or more regions of tissue overlap (block 106 in FIG. 4), processor 80 may compare the score to a threshold score value (134), which may be stored by memory 82 of programmer 14 or a memory of another device. In some examples, the threshold score value may differ depending on whether processor 80 is determining whether there is overlap between the VTA and one or more efficacy regions or one or more adverse-effects regions. For example, processor 80 may compare the score to a first threshold score value to determine whether there is overlap between the VTA and an efficacy region and compare the score to a second threshold score value to determine whether there is overlap between the VTA and an adverse-effects region. In some examples, the first threshold score value may be higher than the second threshold score value.

In some examples, processor 80 may determine that there is overlap between the VTA and one or more first regions (136, as well as "YES" branch of block 106 in FIG. 4) in response to determining the score is greater than (or, in some examples, greater than or equal to) the first threshold score value. The score greater than or equal to the first threshold score value may indicate, for example, that the VTA lays sufficiently within the first region (or multiple first regions) to constitute an overlap. On the other hand, in response to determining the score is less than (or, in some examples, less than or equal to) the first threshold score value, processor 80 may determine that there is no overlap between the VTA and the one or more first regions ("NO" branch of block 106 in FIG. 4).

In some examples in which the voxels of the 3D grid that sit in regions of brain 28 associated with adverse effects of stimulation have negative values, the score computed by processor 80 may be negative or null. Processor 80 may determine that there is overlap between the VTA and the one or more second regions (136, as well as "YES" branch of block 116 in FIG. 4) in response to determining the score is less than (or, in some examples, less than or equal to) the second threshold score value, which may be a negative value in some examples and a positive value in other examples. The score less than or equal to the second threshold score value may indicate, for example, that the VTA sits sufficiently within the second region of tissue to constitute an overlap. On the other hand, in response to determining the score is greater than (or, in some examples, greater than or equal to) the second threshold score value, processor 80 may determine that there is no overlap between the VTA and the second region (136) ("NO" branch of block 116 in FIG. 4).

In some cases, processor 80 (or another processor) updates the voxel values of the 3D grid, e.g., after a first programming session with patient 12, based on the actual experience of patient 12 with one or more sets of electrical stimulation parameter values. For example, if delivery of electrical stimulation by IMD 16 via a selected subset of electrodes 24, 26 and according to a particular set of electrical stimulation parameter values resulted in efficacious electrical stimulation therapy, then processor 80 may increase the values assigned to the voxels that sit within the VTA expected to result from the delivery, by the subset of electrodes 24, 26, of electrical stimulation according to the set of electrical stimulation parameter values. In addition, if delivery of electrical stimulation by IMD 16 via a selected subset of electrodes 24, 26 and according to the set of electrical stimulation parameter values resulted in inefficacious electrical stimulation therapy, adverse effects, or both, then processor 80 may decrease the values assigned to the voxels that sit within the VTA. The effects of the electrical stimulation may be observed by the clinician, reported by patient 12, or determined based on the output of one or more sensors that indicate one or more physiological parameters of patient 12.

The ability to increase or decrease the voxel values based on the results of the actual delivery of electrical stimulation to patient 12 may help generate a patient-specific grid (also referred to herein as a "map"). In addition, to help further personalize the grid to patient 12, the amount by which the voxel values or increased or decreased may be based on patient specific criteria. For example, the decrease in the values of the VTA-overlapping voxels in a given region of tissue associated with adverse effects of stimulation can be greater to the extent that the side-effect associated with that region is one about which patient 12 is particularly concerned, e.g., because patient 12 finds that side-effect particularly intolerable.

In some cases, after updating the voxel values of a grid, processor 80 may update stored therapeutic windows (or just the efficacy threshold and adverse-effects threshold), e.g., by redetermining the therapeutic windows based on an updated grid. In this way, the therapeutic windows stored by memory 82 (or another memory) may be modified over time as the experience of patient 12 with the DBS (or other electrical stimulation therapy) changes over time, as the patient condition changes (e.g., progresses or improves), or both. Again, in some cases, a clinician may interact with programmer 14 to cause processor 80 to determine the therapeutic windows in advance of an in-clinic programming session with patient 12, which may help reduce the amount of time required to program IMD 16.

In other examples of the technique shown in FIG. 5, processor 80 may determine the score based on the extent to which the VTA sits within the one or more regions of tissue. For example, processor 80 may determine whether there is overlap between the VTA and the one or more regions of tissue if, for example, the percentage of the region(s) of tissue covered by the VTA is greater than (or, in some examples, greater than or equal to) a threshold score value. As another example, processor 80 may determine whether there is overlap between the VTA and the one or more regions of tissue if, for example, the number of voxels common to at least one of the regions of tissue and the VTA is greater than (or, in some examples, greater than or equal to) a threshold number. In this example, the voxels of the 3D grid may or may not be associated with respective values.

In examples discussed herein, processor 80 (or a processor of another device, such as IMD 16) may determine the effect of the electrical stimulation delivered by a selected one of electrodes 24, 26 on tissue of patient 12 based on a VTA expected to result from the electrical stimulation delivered by the selected electrode, the electrical stimulation being generated in accordance with a particular set of electrical stimulation parameter values. Processor 80 may determine the VTA by modeling the effects of the electrical stimulation on issue in order to determine the tissue of the patient that will be activated by the electrical stimulation. In some examples, the VTA is defined by the tissue of patient 12 that will be activated by the electrical stimulation.

FIG. 6 is a flow diagram of an example technique for determining a VTA. In accordance with the technique shown in FIG. 6, processor 80 receives patient anatomy data necessary for creating an electrical field model (140). The patient anatomy data indicates one or more characteristics of tissue proximate the selected electrode. The tissue proximate the selected electrode may be identified based on the known location of leads 20 within patient 12 or, if leads 20 are not implanted in patient 12, a target location of leads 20. For example, given a patient's MM and post-operative CT scan, processor 80 can determine the position of lead 20 in brain 28 and, therefore, the anatomical structures proximate the implanted electrodes 24, 26. As another example, given a patient's MM and post-operative CT scan, processor 80 can determine the anatomical structures proximate the target location of electrodes 24, 26 of leads 20, even if leads 20 have not yet been implanted in patient 12.

The patient anatomy data may be specific to or customized for patient 12, or may be more general (e.g., generic physical characteristics of human tissue applicable to a plurality of patients). In some examples, the patient anatomy data includes an anatomical image of target therapy delivery site within patient 12, a reference anatomical image, which may not be specific to patient 12, an anatomical atlas indicating specific structures of the patient's anatomy or a map of the tissue characteristics (e.g., conductivity or density) adjacent to electrodes 24, 26 of leads 20. The patient anatomy data may be created based on data generated by medical imaging, such as, but not limited to, CT, MM, or any other volumetric imaging system. Processor 60 may store the patient anatomy data within section 92 of memory 82 (FIG. 3).

Processor 80 may model the effect of the electrical stimulation delivered by the selected electrode on tissue of patient 12. In the example shown in FIG. 6, processor 80 determines an electrical field model (142) that indicates the electrical field that will propagate away from the electrode when an electrical stimulation signal defined by the set of electrical stimulation parameter values is delivered by the electrode. Processor 80 may, for example, implement an algorithm (e.g., stored as a VTA algorithm 96 in memory 82 of programmer 14) to determine the electrical field model. The algorithm may take the received patient anatomy data into consideration, along with electrical field model equations that define electrical current propagation in order to determine how the electrical current will propagate away from the selected electrode.

Tissue variation within brain 28 (or other site within patient 12) may change the electrical current propagation from the electrode in some directions. These variations may contribute to varying therapeutic windows of electrodes 24, 26 of leads 20. Thus, the electrical field model equations take into consideration the physical tissue characteristics of the tissue adjacent electrodes 24, 26 of leads 20, which is included in the patient anatomy data 92. From this information, processor 80 may estimate an electrical field that will be produced in therapy delivery via the selected electrode when IMD 16 generates an electrical stimulation signal in accordance with the set of electrical stimulation parameter values.

In some examples, processor 80 determines the characteristics (e.g., size, shape, and power distribution) of the electrical field based on generic physical characteristics of human tissue and known physical characteristics of the electrodes 24, 26 of leads 20. However, in some examples, processor 80 determines the characteristics of the electrical field based on the actual anatomical structure of patient 12 being treated. While in either example, the electrical field model may be an approximation of what the electrical field would be in brain 28 of a specific patient 12, the electrical field model determined based on the actual anatomical structure of patient 12 may be a more accurate representation of the electrical field that will result from the delivery of electrical stimulation via the selected electrode.

In the technique shown in FIG. 6, processor 80 determines a neuron model (144). The neuron model indicates, for each of a plurality of volumes of tissue of patient 12, the voltage or current amplitude that is required for the tissue to be stimulated. For example, the neuron model may be a 3D grid of voxels, and each voxel may be associated with a voltage or current amplitude that is required for tissue within the particular voxel to be stimulated. As another example, the neuron model may include a grid of 2D areas, where each area of the grid may be associated with a voltage or current amplitude that is required for tissue within the particular area to be stimulated. In some examples, processor 80 determines the neuron model by generating the neuron model, e.g., based on tissue impedance characteristics of patient 12 determined using medical imaging and stored as patient anatomy data 92 (FIG. 3) or based on tissue impedance characteristics for a general atlas of brain 28. In other examples, the neuron model is predetermined by another processor and stored by memory 82 of programmer 14 (or another memory of another device); processor 80 may determine the neuron model by retrieving it from the memory.

Processor 80 determines an activation field model based on the electrical field model and the neuron model (146). The activation field model may indicate which tissue of patient 12 will be activated (e.g., stimulated) by the electrical field expected to be generated from the delivery of electrical stimulation. In some examples, processor 80 determines the activation field model based on a fit between the neuron model and the electrical field model. The electrical field expected to result from delivery of electrical stimulation by the selected electrode and according to a particular set of electrical stimulation parameters may have an intensity too low to activate the neurons in at least some tissue proximate the selected electrode. Thus, by fitting the neuron model and the electrical field model to each other, processor 80 may determine the volume of tissue that is expected to be activated if electrical stimulation is delivered by the selected electrode to a target tissue location with specified electrical stimulation parameter values.

Figure 7:
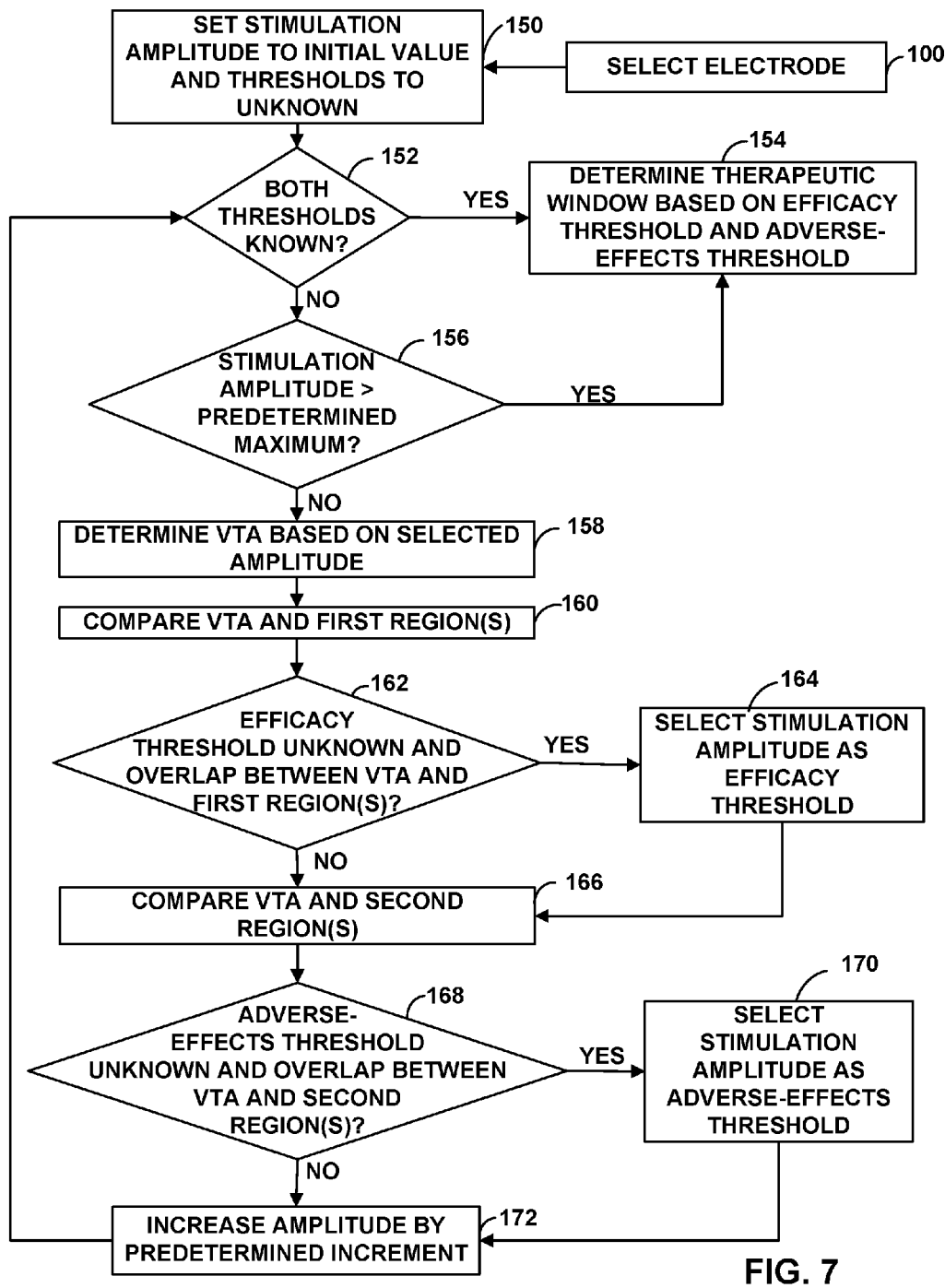
FIG. 7 is a flow diagram illustrating another example technique for determining efficacy and adverse-effects thresholds for at least one electrode of a therapy system.

FIG. 7 is a flow diagram of another example technique that processor 80 may implement to determine therapeutic windows for one or more electrodes 24, 26. FIG. 7 illustrates an example technique for determining the efficacy threshold and adverse-effects threshold for an electrode or electrode combination, and may be an example of the technique shown in FIG. 4.

In the technique shown in FIG. 7, processor 80 selects an electrode 24, 26 (or electrode combination in some examples) (100). Processor 80 selects an initial stimulation amplitude value for determining the thresholds and sets the efficacy threshold and adverse-effects threshold associated with the electrode in memory 82 to unknown (150), such that the selected electrode is not associated with an efficacy threshold or an adverse-effects threshold in memory 82. The initial stimulation amplitude value may be a value known to be less than an efficacy threshold value and an adverse-effects threshold value. For example, in some examples, the initial stimulation amplitude value is zero. Other nominal stimulation amplitude values may also be used as the initial value.

Processor 80 determines whether both the efficacy and adverse-effects thresholds for the selected electrode are known (152). In response to determining both thresholds are known ("YES" branch of block 152), processor 80 determines the therapeutic window for the selected electrode based on the known efficacy and adverse-effects thresholds (154). For example, processor 80 may use the technique described with respect to FIG. 8 to determine the therapeutic window.

On the other hand, in response to determining that it is not true that both thresholds are known ("NO" branch of block 152), processor 80 determines whether the stimulation amplitude is greater than a predetermined maximum (156). The predetermined maximum value for the stimulation amplitude (or other stimulation parameter value or combination of values with which the therapeutic window is defined) can be, for example, stored by memory 82. The predetermined maximum value can be selected using any suitable techniques. In some examples, a clinician may select the predetermined maximum value to be the amplitude value (or other stimulation parameter value or combination of values) at which the stimulation intensity is at a maximum desired intensity for patient 12 or a group of patients. As another example, a clinician may select the predetermined maximum value to be the amplitude value to be the maximum amplitude value permitted by the hardware, software, or both, of IMD 16.

If the stimulation amplitude is greater than the predetermined maximum ("YES" branch of block 156), then processor 80 may cease any further determination of the efficacy and adverse-effects thresholds. To the extent the efficacy threshold is not yet known by the time the stimulation amplitude has been increased to be greater than the predetermined maximum, processor 80 may determine that the efficacy threshold is relatively high and unknown. To the extent the adverse-effects threshold is not yet known by the time the stimulation amplitude has been increased to be greater than the predetermined maximum, processor 80 may determine that the adverse-effects threshold is relatively high. As described with respect to FIG. 8, in some cases, processor 80 may set the adverse-effects threshold to a relatively high value.

In response to determining the stimulation amplitude is greater than (or, in some examples, greater than or equal to) the predetermined maximum ("YES" branch of block 156), processor 80 determines the therapeutic window for the selected electrode based on the efficacy and adverse-effects thresholds that may have already been determined for the selected electrode (154). Processor 80 may use the technique described with respect to FIG. 8 to determine the therapeutic window, even if one of the thresholds may not be known, e.g., because the stimulation amplitude reached the predetermined maximum before the threshold value was reached.

In response to determining the stimulation amplitude is less than or equal to (or, in some examples, less than) the predetermined maximum ("NO" branch of block 156), processor 80 may determine a VTA based on the selected amplitude value (158), e.g., as described above with respect to FIG. 4. Processor 80 compares the VTA and one or more first regions (160) and determines whether the commonality is sufficient or significant enough to constitute an overlap, e.g., using the techniques described with respect to FIG. 5 (162). The commonality of tissue between the VTA and one or more first regions may be sufficient or significant enough to constitute an overlap if, for example, the commonality amounts to at least a predetermined threshold volume when summed. As another example, processor 80 may determine the commonality of tissue between the VTA and one or more first regions is sufficient or significant enough to constitute an overlap in response to determining the score of the voxels that are common to the VTA and the one or more first regions is greater than or equal to a predetermined threshold score.

Processor 80 also determines whether the efficacy threshold value is already known, e.g., has already been determined for the selected electrode (162). For example, processor 80 may determine whether the selected electrode is associated with an efficacy threshold value in memory 82 of programmer 14 (FIG. 3). In response to determining the efficacy threshold is not yet known and there is overlap between the VTA and the one or more first regions ("YES" branch of block 162), processor 80 may select the stimulation amplitude (selected at block 150) as an efficacy threshold (164) and, e.g., store the efficacy threshold and associated electrode as therapeutic window information 98 (FIG. 3) in memory 82.

In response to determining the efficacy threshold for the selected electrode is already known, there is no overlap between the VTA and the one or more first regions, or both ("NO" branch of block 156), or in response to selecting the stimulation amplitude as the efficacy threshold (164), processor 80 may compare the VTA and one or more second regions (166) and determine whether the commonality is sufficient or significant enough to constitute an overlap, e.g., using the techniques described with respect to FIG. 5 (168). The commonality of tissue between the VTA and one or more second regions may be sufficient or significant enough to constitute an overlap if, for example, the commonality amounts to at least a predetermined threshold volume when summed or in response to determining the score of the voxels that are common to the VTA and the one or more second regions is greater than or equal to a predetermined threshold score, or, in some examples, less than or equal to a predetermined threshold score.

In response to determining the adverse-effects threshold is unknown and there is overlap between the VTA and the one or more second regions ("YES" branch of block 168), processor 80 selects the stimulation amplitude (selected at block 102) as the adverse-effects threshold (170) and, e.g., stores the adverse-effects threshold and associated electrode as therapeutic window information 98 (FIG. 3) in memory 82.

In response to determining the adverse-effects threshold is known, there is no overlap between the VTA and the one or more second regions ("NO" branch of block 168), or both, or in response to selecting the stimulation amplitude as the adverse-effects threshold (170), processor 80 increases the amplitude by a predetermined increment (172). Processor 80 may then determine whether both the adverse-effects threshold and efficacy thresholds are known (152) and go through the technique shown in FIG. 7 until the efficacy and adverse-effects threshold values are determined for the selected electrode (152), or until the stimulation amplitude is increased to be greater than the predetermined maximum (156). Processor 80 may also use the technique shown in FIG. 7 to determine the efficacy threshold and adverse-effects thresholds for other electrodes 24, 26 of system.

Figure 8:
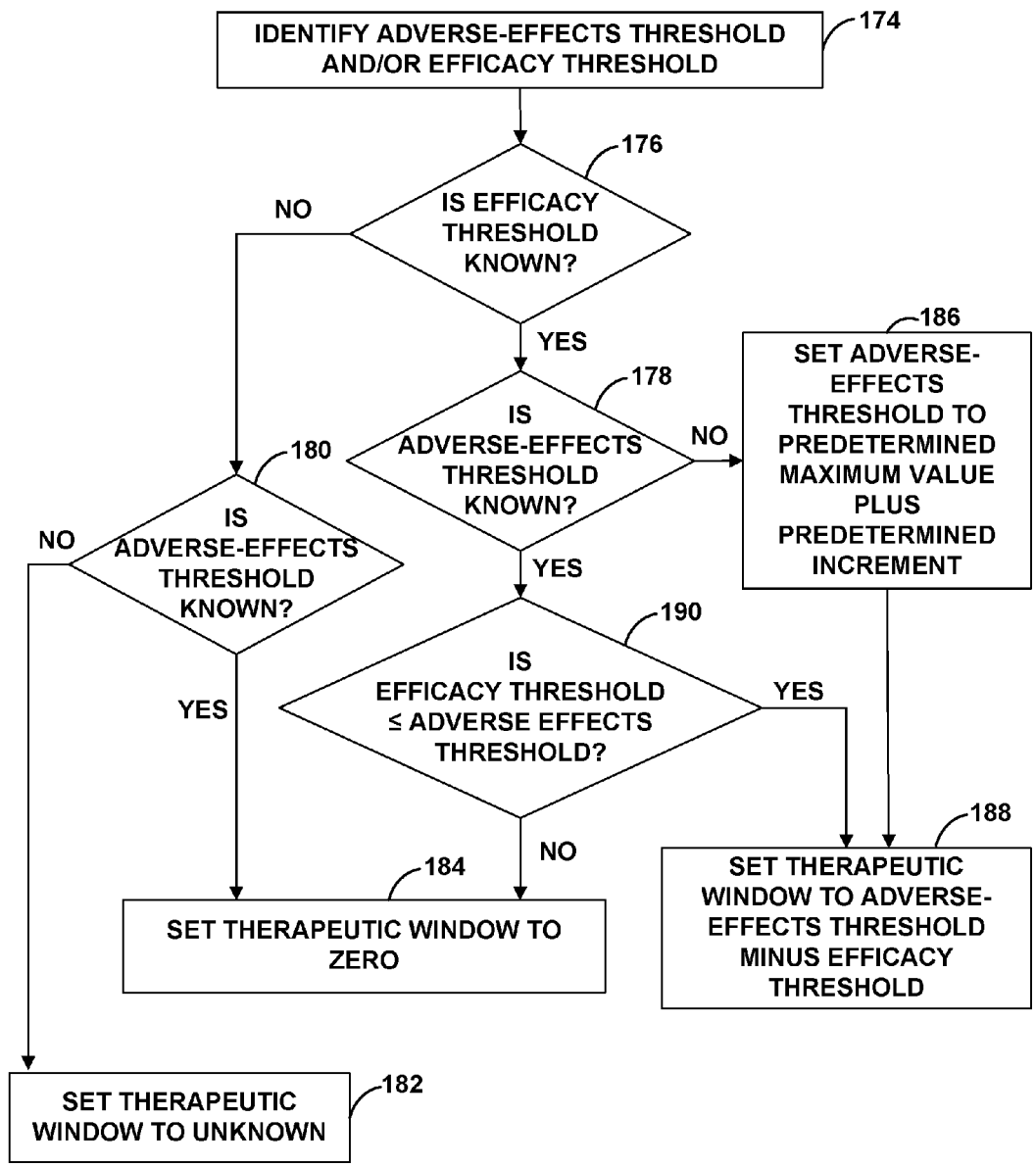
FIG. 8 is a flow diagram illustrating an example technique for determining a therapeutic window for an electrode.

After implementing the technique shown in FIG. 7, processor 80 may determine the therapeutic window for an electrode, e.g., using the technique shown in FIG. 8. FIG. 8 is a flow diagram of an example technique for determining the therapeutic window for an electrode. Processor 80 may implement the technique shown in FIG. 8 for at least one electrode 24, 26, e.g., each electrode 24, 26.

As shown in FIG. 8, in some examples, processor 80 identifies the efficacy threshold, adverse-effects threshold, or both, for a selected electrode 24, 26 (174). For example, processor 80 may determine whether the electrode is associated with an efficacy threshold, adverse-effects threshold, or both in memory 82 of programmer 14. Processor 80 may determine the efficacy threshold, the adverse-effects threshold, or both, and associate the electrode with the determined thresholds in memory 82, e.g., using the one or both techniques described with respect to FIGS. 4 and 7.

Based on the identified thresholds, processor 80 determines, whether the efficacy threshold value is known (176). For example, processor 80 may determine whether the selected electrode is associated with an efficacy threshold in memory 82 of programmer 14 (FIG. 3). In response to determining the efficacy threshold is known ("YES" branch of block 176) or in response to determining the efficacy threshold is not known ("NO" branch of block 176), processor 80 determines whether the adverse-effects threshold is known (178, 180, respectively). As with the efficacy threshold, processor 80 may determine whether the adverse-effects threshold is known based on whether the selected electrode is associated with an adverse-effects threshold in memory 82 of programmer 14 (FIG. 3).

If neither the efficacy threshold nor the adverse-effects threshold are known, processor 80 may determine that the therapeutic window cannot be determined at that time for the selected electrode. Thus, in response to determining the adverse-effects threshold is not known ("NO" branch of block 180), processor 80 sets the therapeutic window for the selected electrode to unknown (182). Processor 80 may associate the selected electrode with the indication of an unknown therapeutic window in memory 82.

If the efficacy threshold was not determined for the electrode, but the adverse-effects threshold was determined, then processor 80 may determine that the therapeutic window for the selected electrode is zero. For example, processor 80 may determine that the selected electrode is not implanted in patient 12 at a location that permits the electrode to deliver efficacious electrical stimulation therapy. The VTA resulting from the electrical stimulation delivered by the electrode may not overlap with any efficacy regions, but may overlap with one or more adverse-effects regions. Thus, in response to determining the adverse-effects threshold is known ("YES" branch of block 180), processor 80 sets the therapeutic window for the selected electrode to zero (184). Processor 80 may associate the selected electrode with a therapeutic window size of zero in memory 82.

If the efficacy threshold is known, but the adverse-effects threshold is not known ("NO" branch of block 178), then processor 80 may determine that the that the selected electrode is not implanted in patient 12 at a location that causes the electrical stimulation delivered by the electrode to cause any side effects. The VTA resulting from the electrical stimulation delivered by the electrode may not overlap with any adverse-effects regions, but may overlap with one or more efficacy regions. Thus, in response to determining the adverse-effects threshold is not known ("NO" branch of block 178), processor 80 sets the adverse-effects threshold to a predetermined maximum value plus a predetermined increment (186).

The predetermined increment can be, for example, the increment with which the stimulation amplitude value was increased in the techniques shown in FIGS. 4 and 7 or another increment value. After setting the adverse-effects threshold (186), processor 80 sets the therapeutic window for the selected electrode based on the known efficacy and adverse-effects thresholds (188). Processor 80 may associate the selected electrode with the therapeutic window in memory 82.

If both the efficacy and adverse-effects thresholds are known ("YES" branch of block 178), then processor 80 may determine whether the efficacy threshold value is less than or equal to the adverse-effects threshold value (190). In response to determining the efficacy threshold value is less than or equal to the adverse-effects threshold value ("YES" branch of block 190), processor 80 sets the therapeutic window for the selected electrode based on the efficacy and adverse-effects threshold values (188). On the other hand, in response to determining the efficacy threshold value is not less than or equal to the adverse-effects threshold value ("NO" branch of block 178), processor 80 sets the therapeutic window to zero (184). In some examples, an efficacy threshold value that is greater than the adverse-effects threshold may indicate that, in order for the delivery of electrical stimulation by the selected electrode to cause one or more efficacious effects, the stimulation may also cause one or more adverse effects.

While the techniques described with respect to FIGS. 4-8 are primarily described as being used to determine a therapeutic window for each individual electrode 24, 26 based on a VTA expected to result from electrical stimulation delivered via the respective individual electrode in a unipolar configuration (e.g., with the housing of IMD 16 acting as a reference electrode), in other examples, the devices, systems, and techniques described herein may be used to determine the therapeutic window for each of a plurality of electrode combinations being defined by select electrodes of electrodes 24, 26. The electrode combinations could be used to, for example, provide bipolar, omnipolar, or multipolar electrical stimulation, or any combination thereof.

For example, rather than selecting a single electrode and determining the therapeutic window based on the VTA resulting from delivery of electrical stimulation with the single electrode in a unipolar combination, processor 80 may select an electrode combination (e.g., a bipolar electrode combination, or an electrode combination including three or more electrodes), and determine the efficacy threshold and adverse-effects threshold based on the VTA expected to result from the delivery of electrical stimulation therapy with the electrode combination (e.g., using the techniques described above) and the set of electrical stimulation parameters. For a particular electrode combination, processor 80 may determine an initial VTA based on a set of electrical stimulation parameter values, and adjust (e.g., increase or decrease in predetermined increments) the value of at least one of the stimulation parameters of the set until the resulting VTA overlaps with one or more efficacy regions of tissue to determine the efficacy threshold for the at least one stimulation parameter. Processor 80 may then continuing adjusting the value of the at least one stimulation parameter (e.g., in predetermined increments) until the resulting VTA overlaps with one or more adverse-effects regions to determine the adverse-effects threshold. The amount of commonality in space between the VTA and the one or more regions of tissue required to constitute an overlap may be the same as that described above with respect to FIGS. 4-8.

Processor 80 may then associate the electrode combination and therapeutic window (or efficacy and adverse-effects threshold values) and store the information in memory 82 of programmer 14 or another memory.

The techniques described herein for associating individual electrodes or electrode combinations with a therapeutic window (or with efficacy and adverse-effects threshold values) may be performed pre-operatively, before leads 20 are implanted in patient 12, or post-operatively, after leads 20 are implanted in patient 12. For example the techniques described with respect to FIGS. 4-8 may be performed before leads 20 are implanted in patient 12, based on a selected target location for the future implantation of leads 20, or after leads 20 are implanted in patient 12, based on the known location of leads 20 within patient 12. Determining the therapeutic windows (or with efficacy and adverse-effects threshold values) before leads 20 are implanted in patient 12 may enable a starting point for programming IMD 16 to be established before leads 20 are even implanted in patient 12.

While the techniques described above are primarily described as being performed by processor 60 of IMD 16 or processor 80 of programmer 14, in other examples, one or more other processors may perform any part of the techniques described herein alone or in addition to processor 60 or processor 80. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
   receiving, by a processor, an input indicative of at least one of an efficacious result or an adverse-effect result of a delivery of electrical stimulation therapy to a patient by a medical device according to at least one electrical stimulation parameter value;
   determining, by the processor, a volume of tissue activation expected to result from the delivery of electrical stimulation to the patient according to the at least one electrical stimulation parameter value;
   determining, by the processor, one or more voxels of a grid that overlap with the volume of tissue activation, wherein the grid comprises a plurality of voxels, and wherein each voxel of the plurality of voxels is associated with a respective voxel value; and
   modifying, by the processor and based on the input, a voxel value of at least one of the one or more voxels of the grid that overlap with the volume of tissue activation.

2. The method of claim 1, wherein the input is based on a sensed physiological signal of the patient.

3. The method of claim 2, wherein the sensed physiological signal of the patient comprises a bioelectrical brain signal of the patient.

4. The method of claim 2, further comprising sensing, by a sensing module, the physiological signal of the patient.

5. The method of claim 1, wherein receiving the input comprises receiving the input via a user interface.

6. The method of claim 1, further comprising controlling the medical device to deliver the electrical stimulation therapy to the patient according to the at least one electrical stimulation parameter value.

7. The method of claim 1, wherein determining, by the processor, the one or more voxels of the grid that overlap with the volume of tissue activation comprises registering, by the processor, the volume of tissue activation to the grid, wherein the grid corresponds to at least one region of a brain of the patient.

8. The method of claim 1, wherein the input is indicative of the efficacious result, and wherein modifying the voxel value comprises increasing the voxel value of the at least one of the one or more voxels based on the input.

9. The method of claim 8, further comprising determining, by the processor, whether the at least one of the one or more voxels is fully within the volume of tissue activation, wherein increasing the voxel value comprises one of increasing the voxel value by a first value based on determining that the at least one of the one or more voxels is fully within the volume of tissue activation, or increasing the voxel value by a second value based on determining that the at least one of the one or more voxels is partially within the volume of tissue activation, wherein the second value is less than the first value.

10. The method of claim 1, wherein the input is indicative of the adverse-effect result, and wherein modifying the voxel value comprises decreasing the voxel value of the at least one of the one or more voxels based on the input.

11. The method of claim 1, further comprising:
    determining, by the processor and after modifying the voxel value, a score based on the values associated with the plurality of voxels of the grid, wherein the score represents an outcome of the electrical stimulation therapy delivered to the patient according to the at least one electrical stimulation parameter value, and
    selecting, by the processor and based on the score, at least one updated electrical stimulation parameter value for the electrical stimulation therapy.

12. The method of claim 11, wherein the input comprises a first input and the volume of tissue activation comprises a first volume of tissue activation, the method further comprising:
    receiving, by the processor, a second input indicative of at least one of an efficacious result and an adverse-effect result of the delivery of electrical stimulation therapy to the patient by the medical device according to the at least one updated electrical stimulation parameter value;
    determining, by the processor, a second volume of tissue activation expected to result from the delivery of electrical stimulation to the patient according to the at least one updated electrical stimulation parameter value;
    determining, by the processor, one or more voxels of the grid that overlap with the second volume of tissue activation; and
    modifying, by the processor and based on the second input, a voxel value of at least one of the one or more voxels of the grid that overlap with the second volume of tissue activation.

13. The method of claim 12, further comprising controlling the medical device to deliver the electrical stimulation therapy to the patient according to the at least one updated electrical stimulation parameter value.

14. The method of claim 1, further comprising selecting, by the processor, the grid from a plurality of grids associated with respective medical conditions, wherein selecting the grid comprises selecting the grid from the plurality of grids based on a medical condition of the patient.

15. The method of claim 1, wherein the volume of tissue activation represents a volume of tissue within a brain of the patient.

16. The method of claim 1, wherein the grid comprises a three-dimensional grid, and wherein each voxel of the plurality of voxels represents a three-dimensional volume of tissue.

17. A system comprising:
a memory that stores a grid comprising a plurality of voxels, wherein each voxel of the plurality of voxels is associated with a respective voxel value; and
a processor configured to:
receive an input indicative of at least one of an efficacious result or an adverse-effect result of a delivery of electrical stimulation therapy to a patient by a medical device according to at least one electrical stimulation parameter value,
determine a volume of tissue activation expected to result from the delivery of electrical stimulation to the patient according to the at least one electrical stimulation parameter value,
determine one or more voxels of the grid that overlap with the volume of tissue activation, and
modify, based on the input, a voxel value of at least one of the one or more voxels of the grid that overlap with the volume of tissue activation.

18. The system of claim 17, wherein the input is based on a sensed physiological signal of the patient.

19. The system of claim 18, wherein the sensed physiological signal of the patient comprises a bioelectrical brain signal of the patient.

20. The system of claim 18, further comprising a sensing module configured to sense the physiological signal of the patient.

21. The system of claim 17, further comprising a user interface, wherein the processor is configured to receive the input via the user interface.

22. The system of claim 17, further comprising the medical device, wherein the processor is further configured to control the medical device to deliver the electrical stimulation therapy to the patient according to the at least one electrical stimulation parameter value.

23. The system of claim 17, wherein the processor is configured to determine the one or more voxels of the grid that overlap with the volume of tissue activation by at least registering the volume of tissue activation to the grid, wherein the grid corresponds to at least one region of a brain of the patient.

24. The system of claim 17, wherein the input is indicative of the efficacious result, and wherein the processor is configured to modify the voxel value by at least increasing the voxel value of the at least one of the one or more voxels based on the input.

25. The system of claim 24, wherein the processor is configured to determine whether the at least one of the one or more voxels is fully within the volume of tissue activation, and increase the voxel value of the at least one of the one or more voxels by one of increasing the voxel value by a first value based on determining that the at least one of the one or more voxels is fully within the volume of tissue activation, or increasing the voxel value by a second value based on determining that the at least one of the one or more voxels is partially within the volume of tissue activation, wherein the second value is less than the first value.

26. The system of claim 17, wherein the input is indicative of the adverse-effect result, and wherein the processor is configured to modify the voxel value by at least decreasing the voxel value of the at least one of the one or more voxels based on the input.

27. The system of claim 17, wherein the processor is further configured to:
determine, after modifying the voxel value of the one or more voxels of the grid that overlap with the volume of tissue activation, a score based on the values associated with the plurality of voxels of the grid, wherein the score represents one of an outcome of the electrical stimulation therapy delivered to the patient according to the at least one electrical stimulation parameter value, and
select, based on the score, at least one updated electrical stimulation parameter value for the electrical stimulation therapy.

28. The system of claim 27, wherein the input comprises a first input and the volume of tissue activation comprises a first volume of tissue activation, wherein the processor is further configured to:
receive a second input indicative of at least one of an efficacious result and an adverse-effect result of the delivery of electrical stimulation therapy to the patient by the medical device according to the at least one updated electrical stimulation parameter value,
determine a second volume of tissue activation expected to result from the delivery of electrical stimulation to the patient according to the at least one updated electrical stimulation parameter value,
determine one or more voxels of the grid that overlap with the second volume of tissue activation, and
modify, based on the second input, a voxel value of at least one of the one or more voxels of the grid that overlap with the second volume of tissue activation.

29. The system of claim 28, further comprising the medical device, wherein the processor is further configured to control the medical device to deliver the electrical stimulation therapy to the patient according to the at least one updated electrical stimulation parameter value.

30. The system of claim 17, wherein the processor is further configured to select the grid from a plurality of grids stored by the memory based on a medical condition of the patient, the plurality of grids being associated with respective medical conditions.

31. The system of claim 17, wherein the volume of tissue activation represents a volume of tissue within a brain of the patient.

32. The system of claim 17, wherein the grid comprises a three-dimensional grid, and wherein each voxel of the plurality of voxels represents a three-dimensional volume of tissue.

33. A system comprising:
means for receiving an input indicative of at least one of an efficacious result or an adverse-effect result of a delivery of electrical stimulation therapy to a patient by a medical device according to at least one electrical stimulation parameter value;
means for determining a volume of tissue activation expected to result from the delivery of electrical stimulation to the patient according to the at least one electrical stimulation parameter value;
means for determining one or more voxels of a grid that overlap with the volume of tissue activation, wherein the grid comprises a plurality of voxels, and wherein each voxel of the plurality of voxels is associated with a respective voxel value; and
means for modifying, based on the input, a voxel value of at least one of the one or more voxels of the grid that overlap with the volume of tissue activation.

34. A non-transitory computer-readable medium comprising instructions that, when executed by a processor, cause the processor to:
receive an input indicative of at least one of an efficacious result or an adverse-effect result of a delivery of electrical stimulation therapy to a patient by a medical device according to at least one electrical stimulation parameter value;

determine a volume of tissue activation expected to result from the delivery of electrical stimulation to the patient according to the at least one electrical stimulation parameter value;

determine one or more voxels of a grid that overlap with the volume of tissue activation, wherein the grid comprises a plurality of voxels, and wherein each voxel of the plurality of voxels is associated with a respective voxel value; and modify, based on the input, a voxel value of at least one of the one or more voxels of the grid that overlap with the volume of tissue activation.

* * * * *